US008501403B2

(12) United States Patent
Molloy et al.

(10) Patent No.: US 8,501,403 B2
(45) Date of Patent: Aug. 6, 2013

(54) AMPLIFICATION OF DNA FRAGMENTS

(75) Inventors: Peter Laurence Molloy, New South Wales (AU); Keith Rand, New South Wales (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 921 days.

(21) Appl. No.: 12/294,891

(22) PCT Filed: Mar. 28, 2007

(86) PCT No.: PCT/AU2007/000389
§ 371 (c)(1),
(2), (4) Date: Jul. 29, 2009

(87) PCT Pub. No.: WO2007/109850
PCT Pub. Date: Oct. 4, 2007

(65) Prior Publication Data
US 2010/0233683 A1    Sep. 16, 2010

(30) Foreign Application Priority Data
Mar. 28, 2006 (AU) .............................. 2006901582

(51) Int. Cl.
C12Q 1/68       (2006.01)
C12P 19/34      (2006.01)
C07H 21/02      (2006.01)
C07H 21/04      (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| 6,200,757 | B1 * | 3/2001 | Kurn et al. | 435/6.11 |
| 6,391,592 | B1 | 5/2002 | Su et al. | |
| 6,794,138 | B1 * | 9/2004 | Cao et al. | 435/6.11 |
| 2005/0214840 | A1 | 9/2005 | Chen | |

FOREIGN PATENT DOCUMENTS

| WO | 94/21820 A1 | 9/1994 |
| WO | 03/012118 A1 | 2/2003 |

OTHER PUBLICATIONS

Patel et al., Formation of chimeric DNA primer extension products by template switching onto an annealed downstream oligonucleotide, Proc. Natl. Acad. Sci. USA, vol. 93, pp. 2969-2974, Apr. 1996, Chemistry.*
Richard A. Guilfoyle, et al., "Ligation-mediated PCR amplification of specific fragments from a Class-II restriction endonuclease total digest", Nucleic Acids Research, 1997, pp. 1854-1858, vol. 25, No. 9.

* cited by examiner

Primary Examiner — Teresa E Strzelecka
(74) Attorney, Agent, or Firm — Sughrue Mion, PLLC

(57) ABSTRACT

A method for detecting a nucleic acid molecule having a target sequence adjacent a 3' terminus is provided. Also provided is a method for differentiating nucleic acid molecules having a target sequence adjacent a 3' terminus from nucleic acid molecules in which the same sequence is embedded within the molecule.

35 Claims, 26 Drawing Sheets

Primer sites for 21qTFMLHC/T and 21qTRC on BstUI-cut DNA

```
                                                      (SEQ ID NO:11) <   ACTCAGGGCCCGTGCCCA 5' 21qTRC
(SEQ ID NO:12)    5' CGGGAGGAATTTAATCTAGAGTCTAACTTGCGTGCCTGGCTGTCCCCACTGAGTCCGGGCACGGGTCAGGGCTAACCG 3'
                  3' GCCCTCCTTAAATTAGATCTCAGATTGAACGCACCGACAGGGGTGACTCAGGGCCCGTGCCCAGTCCGATTGGC 5'
21qTFMLHC/T       CACTCCCACTCGGGAGGAATTTAATCTAGC > (SEQ ID NO:14)
```

Primer sites for 21qTFMLHC/T and 21qTRC on uncut DNA

```
                                                      (SEQ ID NO:11) <   ACTCAGGGCCCGTGCCCA 21qTRC
(SEQ ID NO:15) 5' AGGGCTAACCGCGGGAGGAATTTAATCTAGAGTCTAACTTGCGTGCCTGGCTGTCCCCACTGAGTCCGGGCACGGGTCAGGGCTAACCG 3'
               3' TCCGATTGGCGCCCTCCTTAAATTAGATCTCAGATTGAACGCACCGACAGGGGTGACTCAGGGCCCGTGCCCAGTCCGATTGGC 5'
21qTFMLHC/T       CACTCCCACTCGGGAGGAATTTAATCTAGC > (SEQ ID NO:17)
```

Bases in the primers that match target sequences are shown underlined. Mismatches are shown in bold typeface.

FIGURE 2

Forward end-specific template primer 21qTFMLHC/T

Reverse end-specific template primer 21qTRM13

CACTCCCACTCGGGAGGAATTTAATCTAGC > 21qTFMLHC/T (SEQ ID NO:18)

(SEQ ID NO:19) 5' CGGGAGGAATTTAATCTAGAGTCTAACTTGCGTGGCTGTCCCCACTGAGTCCCGGGCACGGGTCAGGCTAACCG 3'
(SEQ ID NO:20) 21qTRM13 < TTAGTCCGATTGGCTCACACTCCC

FIGURE 4A

HpaII site within Myc gene targeted by mismatch primer.

```
Myc Uncut    5' GAGCCCCAGAGGAGGAACGAGCTAAAACGGAGCTTTTTTGCCCTGCCGTGACCAGATCCCGGAGTTGGAAAA
                                                                            (SEQ ID NO:21)
             MycFC1 CGCCAGAGGAGGAACGAGCTAA 3' >> (SEQ ID NO:22)
Myc HpaII-cut GAGCGCCAGAGGAGGAACGAGCTAAAACGGAGCTTTTTTGCCCTGCCGTGACCAGATCC 3' (SEQ ID NO:23)
                    (SEQ ID NO:24)            << 3' CCCCACTGGTCTACGTCCCTGCTCC  MycRM1
```

FIGURE 5A

| 1 ng HpaII-cut DNA | SYB Ct | SYB Ct | Average SYB Ct | Average Ct Difference |
|---|---|---|---|---|
| K562 (hypomethylated) | 29.0 | 27.8 | 28.4 | |
| CpGenome (Methylated) | 33.9 | 43.3 | 38.6 | 10.2 |
| 34/03 (matched normal) | 27.8 | 27.5 | 27.6 | |
| 35/03 (tumour sample) | 23.6 | 23.7 | 23.6 | 4.0 |
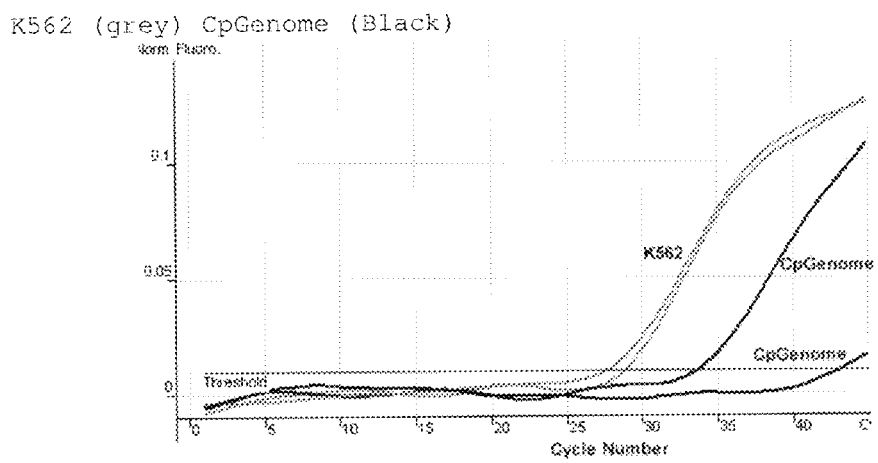
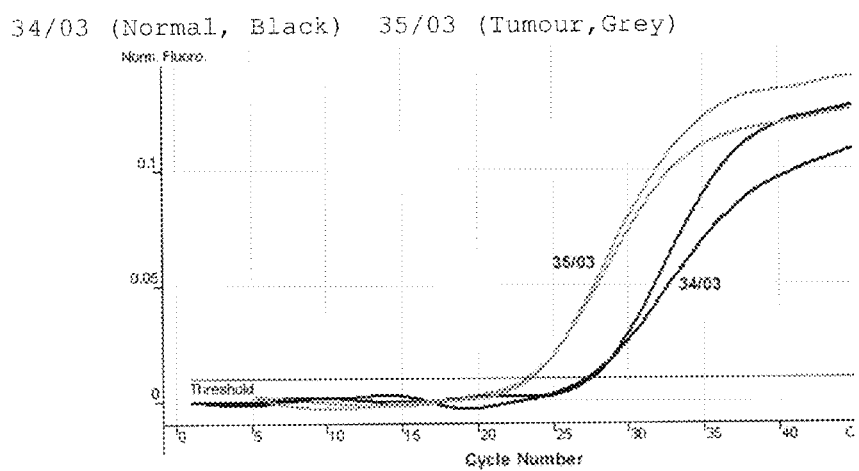
FIGURE 5B

LINE uncut DNA, HpaII sites in bold

```
        (SEQ ID NO:25)        (SEQ ID NO:26)                                        (SEQ ID NO:27)
5'NNNNCCGGTCTACAGCTC----CCAGCGTGAGCGACGCAGAAGACGGGTGATTTCTGCATTT----CCATCTGAGGTACCGGNNNN 3'
3'NNNNGGCCAGATGTCGAG----GGTCGCACTCGCTGCGTCTTCTGCCCACTAAAGACGTAAA----GGTAGACTCCATGGCCNNNN 5'
        (SEQ ID NO:28)        (SEQ ID NO:29)                                        (SEQ ID NO:30)
```

LINE HpaII-cut (and copied)

```
        (SEQ ID NO:31)        (SEQ ID NO:32)                                        (SEQ ID NO:33)
     5'     CGGTCTACAGCTC----CCAGCGTGAGCGACGCAGAAGACGGGTGATTTCTGCATTT----CCATCTGAGGTACCG
     3'     GCCAGATGTCGAG----GGTCGCACTCGCTGCGTCTTCTGCCCACTAAAGACGTAAA----GGTAGACTCCATGGC
        (SEQ ID NO:34)        (SEQ ID NO:35)                                        (SEQ ID NO:36)

HEX  CGACGCAGAAGACGGGTGATTTCTG BH1 5' LPAHex Probe    (SEQ ID NO:37)

CACGCAGGGTCGGTCTACAGCTCgtgCCAGCG  L1FES3-6 >>  (SEQ ID NO:38)
                                   (SEQ ID NO:39)  << L1RE13  CGTAAActgGGTAGACTCCATGGCTCCGACGTCC
```

FIGURE 6A

SYBR Green Results
| | 5 ng DNA | SYB Ct | SYB Ct | Av | Diffn |
|---|---|---|---|---|---|
| 2 | K562 HpaII | 23.3 | 23.0 | 23.2 | 14.9 |
| 4 | CpGen HpaII | 38.6 | 37.5 | 38.1 | |
| 3 | TEX | -- | -- | -- | |
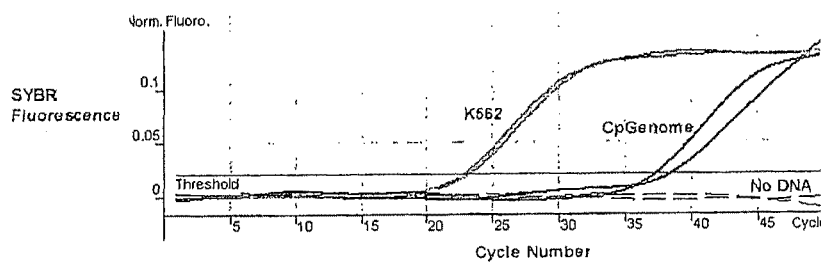
HEX Probe Results
| | 5 ng DNA | HEX Ct | HEX Ct | Av | Diffn |
|---|---|---|---|---|---|
| 2 | K562 HpaII | 26.5 | 26.2 | 26.4 | 14.5 |
| 4 | CpGen HpaII | 41.8 | 40.0 | 40.9 | |
| 3 | TEX | -- | -- | -- | |
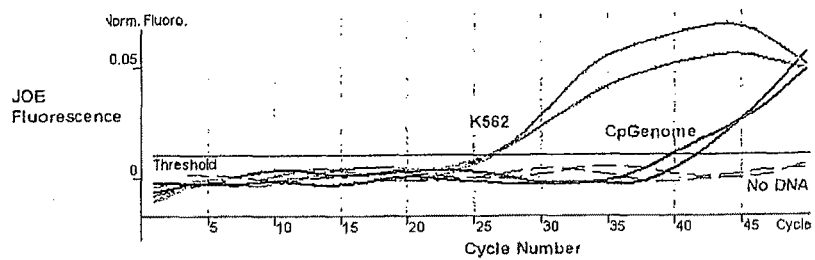
FIGURE 6B

```
JOELUX  CACAGCTTCTCACCATTCCGCCCTGTG >>   (SEQ ID NO:40)

BAFMLJ15    CCATTCCGCCCTGTG TCGGTGGCTCACGCCT Phosphate   (SEQ ID NO:41)

BstUI-Cut target      5' CGGTGGCTCACGCCTGTAATCCCAGCACTTTGGGAGGCCGAGGCGG---  3'
       (SEQ ID NO:42)     3' GCCACCGAGTGCGGACATTAGGGTCGTGAAACCCTCCGGCTCCGC---  5'

(SEQ ID NO:44)    << AluRev21  TCGTGAAACCCTCCGGCTCCG 5'
```

FIGURE 7A

| 1ng DNA | JOE Ct | JOE Ct | Average JOE Ct | Difference |
|---|---|---|---|---|
| K562 (hypomethylated) | 19.3 | 19.7 | 19.5 | |
| CpGenome (Methylated) | 25.7 | 26.1 | 25.9 | 6.4 |
| No DNA control | 33.6 | 33.9 | 33.7 | | hMLH1 Sequence

Uncut DNA  5' -CCAGGGCC GCGG GCTCGCCCGTCCGCCACATACCGCTCCGTAGTATTCGTGTCTCAGCCTCGTAGTGGCCTGACGT -3'
(SEQ ID NO:130)  3' -GGTCCCGG CGCC CGAGCGGGCAGGCGGTGTATGGCGAGGCATCATAAGCACGAGTCGGAGCATCACCGCGGACTGCA -5'

CACAGGTTCTCACCATTCCGCCCTGTG 3' >> JOELUX (SEQ ID NO:122)
MLHJ65 CCATTCCGCCCTGTGTCGCTCGCGGTCCGCCCTTG 3' (SEQ ID NO:131)

GlaI-cut DNA  5'  CGCTCGCCCGTCCGCCACATACCGCTCCGTAGTATTCGTGTCTCAGCCTCGTAGTGGCCTGACGT—
(SEQ ID NO:132)  3'  GCGAGCGGGCAGGCGGTGTATGGCGAGGCATCATAAGCACGAGTCGGAGCATCACCGCGGACTGCA—
                                        (SEQ ID NO:133)  << 3' ATAAGCACGAGTCGGAGCATCACCG MLHRev3 5'

Boxed sequence: GlaI site.
C: C shown in bold, C bases that must be methylated for GlaI to cut efficiently.
Underlined sequence: No match to hMLH1 sequence
--: Sequence continues but is not shown.

FIGURE 8A

Table showing Ct values

|   | DNA | JOE Ct | | | Average Ct | Difference due to GlaI |
|---|---|---|---|---|---|---|
| 1 | CpGenome Fully Methylated DNA + GlaI | 39 | 40 | 37 | 38.6 | 6.0 |
| 2 | CpGenome Fully Methylated DNA, no GlaI | 46 | 42 | 46 | 44.5 | |
| 3 | No DNA control | 48 | 47 | | 47.2 | |
| 4 | Blood DNA + HhaI | 36 | 36 | 37 | 36.1 | 8.4 |

Figure 9A(i)

BRFMX
5' CCTCACAGTAAAAATAGGTGATTTTGGTCTAGCTCTAG> (SEQ ID NO:45)

(SEQ ID NO:46)
CCTCACAGTAAAAATAGGTGATTTTGGTCTAGCTACAGTGAAATCTCGATGGAGTGGGTCCCA
CCTCACAGTAAAAATAGGTGATTTTGGTCTAGCTACAGAGAAATCTCGATGGAGTGGGTCCCA
(SEQ ID NO:129)

Figure 9A(ii)

BRFR1
5' AATGGATCCAGACAACTGTTCAAACT 3' (SEQ ID NO:47)

Figure 9A(iii)

BRAF-T(WT)
CCTCACAGTAAAAATAGGTGATTTTGGTCTAGCTCTAGTGAAATCTCGATGGAGTGGGTCCCA (SEQ ID NO:48)

BRAF-A (Mutant)
CCTCACAGTAAAAATAGGTGATTTTGGTCTAGCTCTAGAGAAATCTCGATGGAGTGGGTCCCA (SEQ ID NO:49)

FIGURE 9A

(SEQ ID NO:50)   BRF2    << ACCCAGGGTAGTCAAACTTG
(SEQ ID NO:51)   BRAF-A  << TCTTTAGAGCTACCTCACCCAGGGTAGTCAAACTTG
                 BRFU  5' CCGCCCTGTGCAGAAATCTCGATGGTTG  (SEQ ID NO:52)
JOELUX 5' CACAGGTTCTCACCATTCGCCCTGTG >> (SEQ ID NO:53)

FIGURE 9B

Fig.10A(i) *Restriction enzyme cleavage*

```
              (SEQ ID NO:54)         (SEQ ID NO:55)
Short sequence  ..GAAGACACTTTTT-3'.....TTTTTTTCAGCCTTCTG..
                ..CTTCTGTGAAAAAAAA. ...3'-AAAGTCGGAAGTC..
              (SEQ ID NO:56)         (SEQ ID NO:57)

(SEQ ID NO:58)         (SEQ ID NO:59)
Long sequence   ..GAAGACACTTTTT-3'      TTTTTTTTTCAGCCTTCTG..
                ..CTTCTGTGAAAAAAAA      3'-AAAAAAGTCGGAAGTC..
              (SEQ ID NO:60)         (SEQ ID NO:61)
```

Fig. 10A(ii) *Terminal transferase (bottom strand)*

Short sequence    3'-TTTTTTTTTTAAAGTCGGAAGTC..(SEQ ID NO:62)

Long sequence     3'-TTTTTTTTTTAAAAAAGTCGGAAGTC.. (SEQ ID NO:63)

Fig. 10A(iii) *Selective priming*

```
Short sequence   3'-TTTTTTTTTTAAAGTCGGAAGTC..(SEQ ID NO:64)
                        5' AAAAAAAAAATTTCAG>  priming  (SEQ ID NO:65)
Long sequence    3'-TTTTTTTTTTAAAAAAGTCGGAAGTC.. (SEQ ID NO:66)
                        5' AAAAAAAAAATTTCAG>  no priming (SEQ ID NO:67)
```

Fig. 10A(iv) ES-PCR

```
Short sequence    3'--               <AAAGTCGGAAGTC.. (SEQ ID NO:68)
Template oligo    5' ACCATTCCGCCCTGTGCGGATTTCAGCCTTCAG-NH2  (SEQ ID NO:69)

Long sequence     3'--             AAAAAAGTCGGAAGTC..(SEQ ID NO:70)
Template oligo    5' ACCATTCCGCCCTGTGCGGATTTCAGCCTTCAG-NH2..(SEQ ID NO:69)
```

Ten Ts (SEQ ID NO:71):

CCGCGTTATCCGACCAGGC`TTTTTTTTTT`CCTTCATAATGCACTTTGGAGAAGCAGCA....
GGCGCAATAGGCTGGTCCGAAAAAAAAAAGGAAGTATTACGTGAAACCTCTTCGTCGT....

Nine Ts (SEQ ID NO:73):

CCGCGTTATCCGACCAGGC`TTTTTTTTT`CCTTCATAATGCACTTTGGAGAAGCAGCA....
GGCGCAATAGGCTGGTCCGAAAAAAAAAGGAAGTATTACGTGAAACCTCTTCGTCGT....

Fig. 10B(ii)

3' termini generated when cut with MmeI:

```
Ten       5'    ATAATGCACTTTGGAGAAGCAGCA....(SEQ ID NO:75)
          3'    AGTATTACGTGAAACCTCTTCGTCGT....(SEQ ID NO:76)

Nine      5'    TAATGCACTTTGGAGAAGCAGCA....(SEQ ID NO:77)
          3'    GTATTACGTGAAACCTCTTCGTCGT....(SEQ ID NO:78)
```

Fig. 10B(iii)

```
     linker
     (SEQ ID NO:79)         (SEQ ID NO:80)
     CACCGACCGTCGAGCA       TAATGCACTTTGGAGAAGCAGCA....
     GTGGCTGGCAGCTC         GTATTACGTGAAACCTCTTCGTCGT....
     (SEQ ID NO:81)         (SEQ ID NO:82)
```

Forward primer
CACCGACCGTCGAGTCATAATG  (SEQ ID NO:83)

FIGURE 10B

```
            3' AGTATTACGTGAAACCTCTTCGTCGT (SEQ ID NO:84)
      5' ACCATTCCGCCCTGTGCGGAACATAATGCACTTTG-NH2 (SEQ ID NO:85)

3' <GTATTACGTGAAACCTCTTCGTCGT....(SEQ ID NO:86)
5' ACCATTCCGCCCTGTGCGGAACATAATGCACTTTG-NH2  (SEQ ID NO:85)
```

FIGURE 10C

Figure 11A(i): NR22 microsatellite region:

(SEQ ID NO:88)
5' GAAGATTTTTTTTTTTTTTTTTTTTTAATATGCAGTTTGTAAGAACAAAACTGGATGGCATCAG
3' CTTCTAAAAAAAAAAAAAAAAAAAAAATTATACGTCAAAC<u>ATTCTTGTTTTGACCTACCGTAGTC</u>
    MboII                                                                 Reverse primer site NR22R1

Figure 11A(ii): Annealing to control template oligo F1NR22-0:

```
22   (SEQ ID NO:89)      3' AAAAAAAAAAAAAATTATACGTCAAACATTCTTGTTTTGACCTACCGTAGTC
     5' CAGATCCTCTTCCTCCGTGAGTTTTTTTTTTTTTTAATATGCAGTTTGGUUC 3' (SEQ ID NO:90)

20   (SEQ ID NO:91)        3' AAAAAAAAAAAAATTATACGTCAAACATTCTTGTTTTGACCTACCGTAGTC
     5' CAGATCCTCTTCCTCCGTGAGTTTTTTTTTTTTTTAATATGCAGTTTGGUUC 3' (SEQ ID NO:90)

18   (SEQ ID NO:93)          3' AAAAAAAAAAAATTATACGTCAAACATTCTTGTTTTGACCTACCGTAGTC
     5' CAGATCCTCTTCCTCCGTGAGTTTTTTTTTTTTTTAATATGCAGTTTGGUUC 3' (SEQ ID NO:90)

16   (SEQ ID NO:95)             3' AAAAAAAAAATTATACGTCAAACATTCTTGTTTTGACCTACCGTAGTC
     5' CAGATCCTCTTCCTCCGTGAGTTTTTTTTTTTTTTAATATGCAGTTTGGUUC 3' (SEQ ID NO:90)

5' CACGGTCCAGATCCTCTTCCTCCGTG >>  FAMLUX1        (SEQ ID NO:97)
```

Figure 11A(iii): Annealing to test template oligo J5NR22-4:

```
22   (SEQ ID NO:89)      3' AAAAAAAAAAAAAATTATACGTCAAACATTCTTGTTTTGACCTACCGTAGTC
        5' GGCTGGACGCATCGTAGAGTTTTTTTTTTAATATGCAGTTTGGUUC 3' (SEQ ID NO:99)

20   (SEQ ID NO:91)        3' AAAAAAAAAAAAATTATACGTCAAACATTCTTGTTTTGACCTACCGTAGTC
        5' GGCTGGACGCATCGTAGAGTTTTTTTTTTAATATGCAGTTTGGUUC 3' (SEQ ID NO:99)

18   (SEQ ID NO:93)          3' AAAAAAAAAAAATTATACGTCAAACATTCTTGTTTTGACCTACCGTAGTC
        5' GGCTGGACGCATCGTAGAGTTTTTTTTTTAATATGCAGTTTGGUUC 3' (SEQ ID NO:99)

16   (SEQ ID NO:95)             3' AAAAAAAAAATTATACGTCAAACATTCTTGTTTTGACCTACCGTAGTC
        5' GGCTGGACGCATCGTAGAGTTTTTTTTTTAATATGCAGTTTGGUUC 3' (SEQ ID NO:99)

5' CTACGAGTGGCTGGACGCATCGTAG >>  JOELUX5 (SEQ ID NO:106)
```

FIGURE 11A

11B(i)
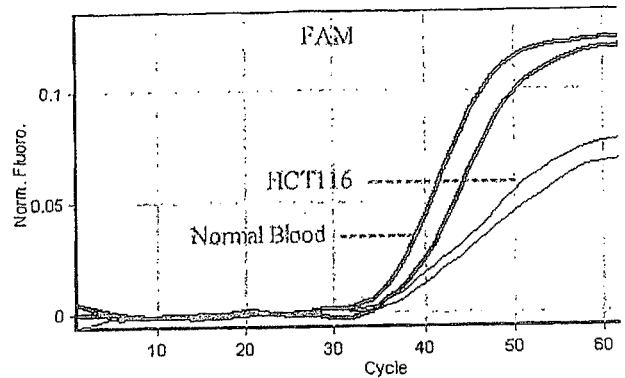
11B(ii)
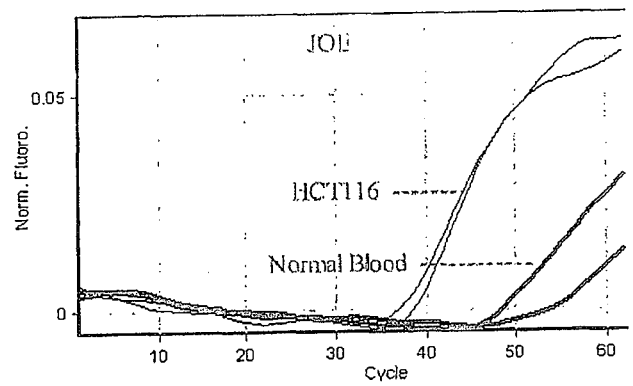
FIGURE 11B

```
Normal                              3' CCGAGTGCGGACATTAGGGTTAGAAGAGGC 5' (SEQ ID NO:113)
Insert 1bp                          3' ACCGAGTGCGGACATTAGGGTTAGAAGAGGC 5' (SEQ ID NO:114)
Insert 4bp                          3' GCCACCGAGTGCGGACATTAGGGTTAGAAGAGGC 5' (SEQ ID NO:115)

Template Oligonucleotide CCATTCCGCCCTGTGTCGGTggcuCACGCCTGTAATCCCTUUG 3' (SEQ ID NO:116)
JOELUX   5'  CACAGGTTCTCACCATTCCGCCCTGTG >>              << TTAGAAGAGGCGGAGCGGAG 5' CommR5
                    (SEQ ID NO:117)                                      (SEQ ID NO:118)
```

Oligonuclseotides used in Example 8.2.
2' O-Methyl nucleotides in the template oligonucleotide are underlined as are the DNA nucleotides in the cut DNA that hybridize to them.

FIGURE 12B

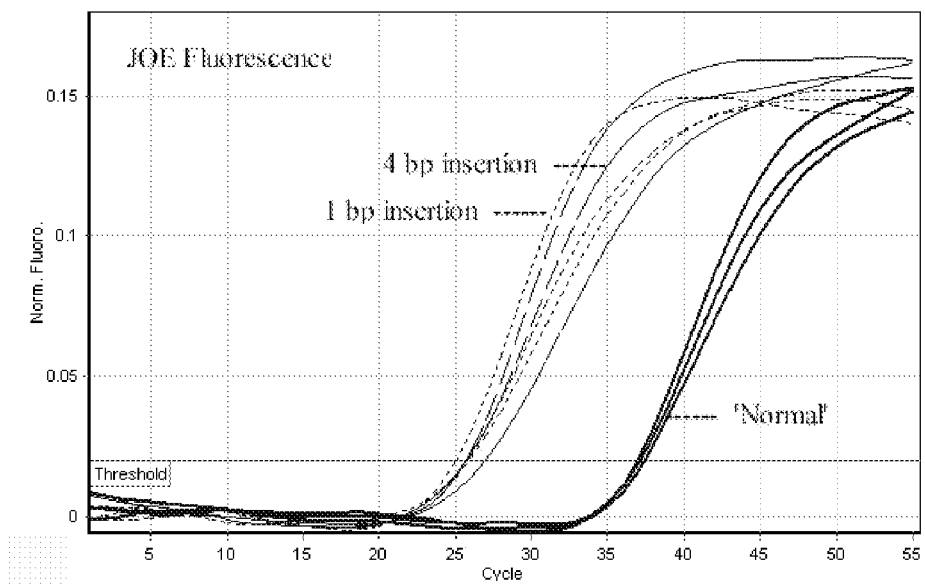

FIGURE 12C

```
                                    (SEQ ID NO:119) AluRev <<TCGTGAAACCCTCCGGCTCCG 5'
(SEQ ID NO:120)Uncut    3' TTTTTGCCACCGAGTGCGGACATTAGGGTCGTGAAACCCTCCGGCTCCGCC 5'
(SEQ ID NO:121)Cut      3'      GCCACCGAGTGCGGACATTAGGGTCGTGAAACCCTCCGGCTCCGCC 5'
AluPhB      5' CCATTCCGCCCTGTGTCGGTGGCTCACGCCTGTAATCCCP 3'    (SEQ ID NO:123)
5' cacaggTTCTCACCATTCCGCCCTGTG >>      JOELUX  (SEQ ID NO:122)
```

FIGURE 13A

```
AluPhB      CCATTCCGCCCTGTGTCGGTGGCTCACGCCTGTAATCCC 3' phosphate (SEQ ID NO:123)
AluMeAm     CCATTCCGCCCTGTGTCgGTGGCTCACGCCTGTAATCCC 3' C7-amine  (SEQ ID NO:124)
AluAbSp     CCATTCCGCCCTGTGTCGXTGGCTCACGCCTGTAATCCC 3' C3 spacer (SEQ ID NO:125)
AluHL       CCATTCCGCCCTGTGTCGGTGGCTCACGCCTGGCGGAATGG 3'(SEQ ID NO:126)
AluMeMult   CCATTCCGCCCTGTGTCgguggCTCACGCCTGTAATCCC 3' C7-amine  (SEQ ID NO:127)
AluUUG      CCATTCCGCCCTGTGTCGGUUGCTCACGCCTGTAATCCCTUUG 3'      (SEQ ID NO:128)
```

FIGURE 13B

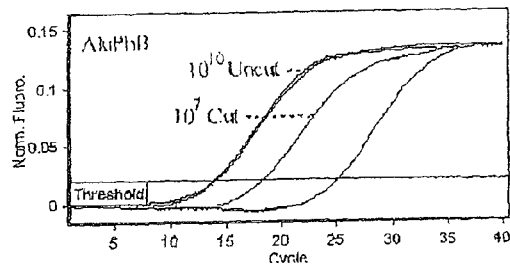
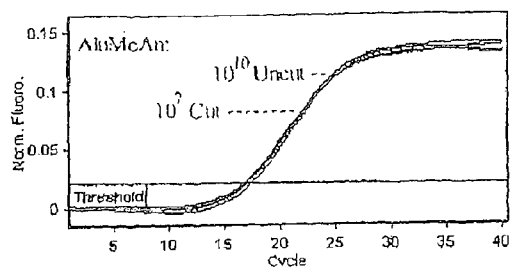
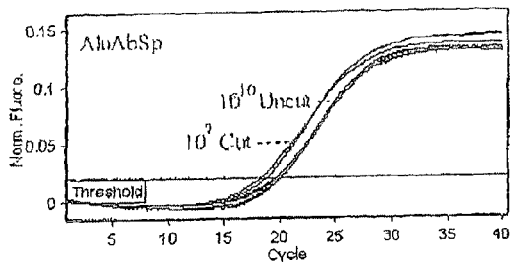
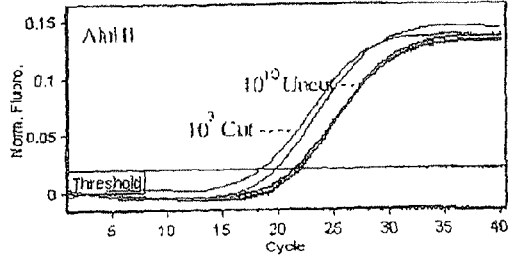
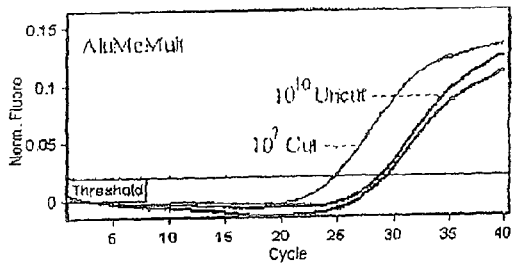
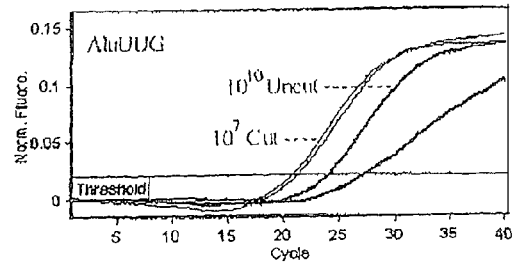
FIGURE 13C

AMPLIFICATION OF DNA FRAGMENTS

FIELD OF INVENTION

The invention relates to differentiating nucleic acid molecules having a specific sequence adjacent a 3' terminus from nucleic acid molecules in which the same sequence is embedded within the molecule or is absent. The invention also relates to differentiating nucleic acid molecules that differ in the sequence adjacent a 3' terminus. In particular, the invention relates to a method for selective amplification of cleaved DNA in the presence of uncleaved DNA sharing the same target sequence.

BACKGROUND OF THE INVENTION

The polymerase chain reaction (PCR) is based on repeated cycles of denaturation of double stranded DNA, followed by oligonucleotide primer annealing to the DNA template, and primer extension by a DNA polymerase (eg see Mullis et al U.S. Pat. Nos. 4,683,195, 4,683,202 and 4,800,159). The oligonucleotide primers used in PCR are designed to anneal to opposite strands of the DNA, and are positioned so that the DNA polymerase-catalysed extension product of one primer can serve as a template strand for the other primer. The PCR amplification method results in the exponential increase of discrete DNA the length of which is defined by the 5' ends of the oligonucleotide primers.

In its standard application, primers are chosen that match sequences within the target genome and flank the region of DNA that is to be amplified. Additionally a number of variations of PCR have been described in which linkers are ligated onto the ends of DNA fragments and sequences in the linkers are then used for priming DNA amplification. Ligation-mediated PCR was first applied to DNA footprinting and sequencing reactions where the DNA ends were generated by DNaseI digestion or chemical cleavage (Mueller and Wold, 1989 and Pfeifer et al. 1989) and extended to ends formed by restriction digestion (Steigerwald et al. 1990). Specificity is achieved by combining primers to a specific target region with primers targeted to the added linker. Variations of the technique have found a range of uses in genome sequencing and DNA methylation analysis, chromosome walking, identifying sites of chromosome integration or recombination, studying mutation breakpoints and mRNA termini. Ligation-mediated PCR can also be used for whole genome amplification, where the entire population of molecules with ligated ends is amplified (Schumaker et al., 2006).

Despite the wide-ranging usefulness of ligation-mediated PCR, there is an ongoing need for improved PCR-based methodologies that allow for selective amplification of DNAs having 3' ends and that provide advantages of simplicity, specificity and expediency.

SUMMARY OF THE INVENTION

The present invention provides methods for differentiating a nucleic acid molecule having a specific sequence adjacent a 3' terminus from nucleic acid molecules in which the same target sequence is present but embedded within the molecule, or is absent. The 3' termini may be the result of, for example, restriction enzyme cleavage or other specific enzymatic or chemical cleavage, or the termini may be the free ends of PCR-generated amplicons, the free ends of a naturally occurring DNA such as from a chromosome, virus or phage, or the termini may be produced by reverse transcription from an RNA template, or produced by any other means that generates nucleic acids having a 3' terminus.

According to one embodiment of the invention, also referred herein to as 'end-specific PCR' or ES-PCR, nucleotide sequences located adjacent to a 3' terminus of a nucleic acid molecule are utilised in priming amplification reactions that proceed only when these sequences occur adjacent to a 3' terminus, rather than when these sequences are embedded within nucleic acid molecules.

To achieve this differentiation, an oligonucleotide (hereinafter "template oligonucleotide") is utilised having a 3' portion complementary to the target sequence and a 5' portion that forms a 5' tail when the oligonucleotide anneals to nucleic acid. When the template oligonucleotide anneals to target sequence located adjacent a 3' terminus, copying of the 5' tail in the presence of a suitable polymerase by extension of the free 3' terminus can take place. When the template oligonucleotide anneals to target sequence that is embedded within a nucleic acid molecule, copying of the 5' tail cannot occur, due to the absence of a free 3' terminus. The presently described oligonucleotide is referred to herein as the template oligonucleotide due to its 5' tail serving as a template for 3' extension of the target sequence located adjacent a 3' terminus.

The copying of the 5' tail when the target sequence occurs adjacent to a 3' terminus results in the addition of new sequence to the 3' end of the targeted nucleic acid molecule, which can be utilised in subsequent selective amplification of nucleic acid molecules having the target sequence adjacent to the 3' terminus.

For example, where a 3' terminus is a product of restriction enzyme cleavage, selective amplification of cleaved DNA over uncleaved DNA will occur.

In one embodiment, the template oligonucleotide incorporates a modification that delays 3' extension of the oligonucleotide, whilst copying of its 5' tail by extension of the target sequence proceeds without hindrance. Accordingly, the nucleic acid sequence of the 3' region of the template oligonucleotide may be chosen such that hybridization to the target sequence will be unstable at the conditions used so that in the absence of copying of the 5' tail, hybridization of the template oligonucleotide to target sequence embedded within a nucleic acid molecule is inhibited. Copying of the 5' tail enhances annealing of the template oligonucleotide to the target sequence adjacent to a 3' terminus compared with annealing of the template oligonucleotide to target sequence embedded within a nucleic acid molecule, in which no copying of the 5' tail occurs.

Enhanced annealing of the template oligonucleotide in turn increases efficiency with which 3' extension of the template oligonucleotide occurs, thereby enabling amplification of the target sequence to proceed, either in combination with another template oligonucleotide priming in the reverse direction, or with a reverse primer complementary to sequences elsewhere within the targeted nucleic acid molecule, to allow specific detection or amplification of the desired molecule, i.e. that having the target sequence adjacent to a 3' terminus.

The newly incorporated sequence at the 3' terminus of a targeted nucleic acid molecule (by copying of the 5' tail of the oligonucleotide) can also be utilised to amplify the targeted nucleic acid molecule.

Therefore, in one embodiment of the invention, a sample is incubated with a template oligonucleotide the 3' portion of which contains sequences substantially complementary to target sequence adjacent the 3' terminus of the targeted nucleic acid molecule, and the 5' portion forming a 5' tail. The template oligonucleotide incorporates a modification that delays extension from its 3' terminus. In the presence of a suitable polymerase, the 5' tail of the template oligonucleotide is copied by extension of the target sequence from its 3' terminus. As a result of 3' extension of the target sequence, annealing of the template oligonucleotide is enhanced compared with its annealing to target sequence embedded within a nucleic acid molecule, therefore promoting 3' extension of the template oligonucleotide when it is annealed to target sequence adjacent to a 3' terminus. The template oligonucleotide itself or the newly incorporated sequence (referred to herein as the "third oligonucleotide") can then be used alone or in combination with sequences within the targeted molecule to allow specific detection or amplification of the desired target sequences, ie those adjacent to a 3' terminus.

Methods of the present invention differ from ligation-mediated PCR in that no ligation step is necessary and sequence specificity is directly incorporated into the template oligonucleotides that are targeted to the nucleic acid 3' termini.

Accordingly, one aspect of the present invention provides a method for selective amplification from a sample of a nucleic acid molecule having a target sequence adjacent a 3' terminus, in the presence of molecules comprising the target sequence not adjacent a 3' terminus but embedded within the molecule, the method comprising
(i) contacting the sample with a template oligonucleotide having
(a) a 3' region substantially complementary to the target sequence adjacent the 3' terminus of a nucleic acid molecule;
(b) a 5' tail comprising a nucleic acid sequence such that a free 5' tail is formed when the template oligonucleotide anneals to the target sequence located adjacent a 3' terminus or embedded within a nucleic acid molecule, the 5' tail providing a template for extension of the 3' terminus of the target sequence incorporating sequence complementary to the 5' tail of the template oligonucleotide resulting in the addition of sequence complementary to the 5' tail to the target sequence; and
(c) a modification in the 3' region that delays 3' extension of said template oligonucleotide;
(ii) contacting the sample with a second oligonucleotide for priming in a reverse direction to the template oligonucleotide, and optionally a third oligonucleotide sharing nucleotide sequence with the 5' tail of the template oligonucleotide; and
(iii) carrying out amplification of the sample wherein
(a) annealing of the template oligonucleotide to target sequence adjacent a 3' terminus is stabilised over annealing of said oligonucleotide to target sequence not adjacent to a 3' terminus by copying of the 5'tail of the template oligonucleotide by extension from the 3' terminus of the target sequence in the presence of delayed 3' extension of said oligonucleotide; and
(b) consequent stabilised annealing of the template oligonucleotide to target sequence adjacent to a 3' terminus enhances efficiency of 3' extension of the template oligonucleotide compared to extension of the template oligonucleotide annealed to target sequence not adjacent a 3' terminus, and
(c) amplification occurs using the template oligonucleotide and/or the third oligonucleotide in combination with the second oligonucleotide, resulting in selective amplification of target sequence adjacent to a 3' terminus in the presence of nucleic acid molecules comprising target sequence embedded within the molecule.

The nucleic acid molecules may be DNA (including cDNA) or RNA, or may be molecules comprising a combination of deoxyribonucleotides, ribonucleotides and/or analogues of natural nucleotides.

In accordance with methods of the present invention, selective amplification of cleaved nucleic acid molecules in the presence of uncleaved DNA nucleic acid molecules sharing the same target sequence can be achieved, wherein as the result of cleavage, the target sequence is adjacent a 3' terminus.

Accordingly, a further aspect of the present invention provides a method for selective amplification from a sample, of a nucleic acid molecule having a target sequence adjacent a 3' terminus the result of cleavage of the molecule, in the presence of uncleaved molecules comprising the target sequence embedded within the molecule, the method comprising:
(i) contacting the sample with a template oligonucleotide having
(a) a 3' region substantially complementary to the target sequence adjacent the 3' terminus of a nucleic acid molecule;
(b) a 5' tail of comprising a nucleic acid sequence such that a free 5' tail is formed when the template oligonucleotide anneals to cleaved or uncleaved nucleic acid molecules, the 5' tail providing a template for extension of the 3' terminus of the target sequence incorporating sequence complementary to the 5' tail of the template oligonucleotide resulting in the addition of sequence complementary to the 5' tail to the target sequence; and
(c) a modification in the 3' region that delays 3' extension of the template oligonucleotide;
(ii) contacting the sample with a second oligonucleotide for priming in a reverse direction to the template oligonucleotide, and optionally a third oligonucleotide sharing nucleotide sequence with the 5' tail of the template oligonucleotide; and
(iii) carrying out amplification of the sample wherein
(a) annealing of the template oligonucleotide to target sequence adjacent a 3' terminus the result of cleavage of a nucleic acid molecule, is stabilised over annealing of said oligonucleotide to target sequence not adjacent a 3' terminus in an uncleaved nucleic acid molecule by copying of the 5' tail of the template oligonucleotide by extension from the 3' terminus of the target sequence in the presence of delayed 3' extension of said oligonucleotide; and
(b) consequent stabilised annealing of the template oligonucleotide to the cleaved nucleic acid molecule enhances efficiency of 3' extension of the template oligonucleotide compared to extension of said oligonucleotide annealed to an uncleaved nucleic acid molecule, and
(c) amplification occurs using the template oligonucleotide and/or the third oligonucleotide in combination with the second oligonucleotide, resulting in selective amplification of target sequence adjacent to a 3' terminus over target sequence embedded within a nucleic acid molecule, resulting in selective amplification of cleaved nucleic acid molecules over uncleaved nucleic acid molecules.

In one embodiment, cleaved and uncleaved nucleic acid molecules are DNA molecules.

In addition to the differentiation of nucleic acid molecules having target sequence adjacent a 3' terminus from nucleic acid molecules having target sequence embedded within the molecule, the template oligonucleotide permits differentiation between nucleic acid molecules that differ in sequence adjacent the 3' terminus i.e. differentiation between 3' termini. This is by virtue of the template oligonucleotide comprising at the 3' region nucleotide sequence specific to a target sequence, as is usually the case for sequence-specific oligonucleotide primers. Thus, selection of the target sequence adjacent a 3' terminus from the various 3' termini in a sample is achieved. Notably, due to the formation of a 5' tail when the template oligonucleotide anneals to a nucleic acid molecule, mismatches between the template oligonucleotide and the nucleic acid sequence adjacent a 3' terminus will hinder copying of the 5' tail, as extension of the 3' terminus of the target DNA sequence will be hindered. This arrangement can be utilised to design template oligonucleotides that will not only distinguish target sequence adjacent a 3' terminus from embedded target sequence (via the 5' tail), but that will also distinguish between 3' termini where variations in sequence adjacent the 3' terminus exist.

Accordingly, a further aspect of the present invention provides a method for selective amplification from a sample, of a nucleic acid molecule having a target sequence adjacent a 3' terminus, in the presence of a mixed population of 3' termini, the method comprising
  (i) contacting the sample with a template oligonucleotide having
    (a) a 3' region substantially complementary to the target sequence adjacent the 3' terminus;
    (b) a 5' tail comprising a nucleic acid sequence such that a free 5' tail is formed when the template oligonucleotide anneals to the target sequence adjacent a 3' terminus, the 5' tail providing a template for extension of the 3' terminus of the target sequence incorporating sequence complementary to the 5' tail of the template oligonucleotide resulting in the addition of sequence complementary to the 5' tail to the target sequence; and
    (c) a modification in the 3' region that delays 3' extension of said oligonucleotide;
  (ii) contacting the sample with a second oligonucleotide for priming in a reverse direction to the template oligonucleotide, and optionally a third oligonucleotide sharing nucleotide sequence with the 5' tail of the template oligonucleotide; and
  (iii) carrying out amplification of the sample wherein
    (a) specific annealing of the template oligonucleotide to target sequence adjacent a 3' terminus is stabilised over annealing of template oligonucleotide to non-complementary sequence adjacent a 3' terminus, by copying of the 5' tail of the template oligonucleotide by extension from the 3' terminus of the target sequence in the presence of delayed 3' extension of the template oligonucleotide; and
    (b) consequent stabilised annealing of the template oligonucleotide to the target sequence adjacent a 3' terminus enhances efficiency of 3' extension of the template oligonucleotide compared to extension of said oligonucleotide annealed to non-complementary sequence adjacent a 3' terminus, and
    (c) amplification occurs using the template oligonucleotide and/or the third oligonucleotide in combination with the second oligonucleotide, resulting in selective amplification of target sequence adjacent to a 3' terminus in the presence of a mixed population of 3' termini.

In one embodiment the nucleic acid molecules are DNA molecules.

The template oligonucleotide may include modified bases within its 3' region which when hybridized at the 3' terminus of a nucleic acid molecule will block 3' extension of that molecule.

Preferably, the 3' modification that delays 3' extension of the template oligonucleotide includes the incorporation of a 3' terminal nucleotide mismatch, a deletion or an insertion in the 3' region of the template oligonucleotide close to the 3' terminus, a combination of these, or any other modification that results in delayed 3' extension of the template oligonucleotide.

Copying of the 5' tail by extension of the 3' terminus of the target sequence leads to selective amplification of the nucleic acid molecule having target sequence located adjacent to a 3' terminus. In the absence of copying of the 5' tail, 3' extension of the annealed template oligonucleotide either does not occur or occurs at an insignificant rate due to the modification in the 3' region of the template oligonucleotide that delays or hinders 3' extension, destabilising annealing of the template oligonucleotide. Therefore, copying of the 5' tail will enhance annealing and thereby increase the efficiency of 3' extension of the template oligonucleotide.

Selective amplification of target sequence located adjacent a 3' terminus can also be achieved by blocking 3' extension of the template oligonucleotide. Where a template oligonucleotide is blocked from 3' extension, an additional, third, oligonucleotide that shares sequence with the 5' tail of the template oligonucleotide is utilised in the amplification reaction so as to allow thermocyclic amplification to proceed. Thus, 3' extension of the template oligonucleotide that is annealed to target sequence embedded within a nucleic acid molecule cannot occur because extension is blocked but more importantly because no copying of the 5' tail takes place, and, consequently, amplification of nucleic acid using the third oligonucleotide will not amplify target sequence located within a nucleic acid molecule.

A variation of the method in which 3' extension of the template oligonucleotide can occur, but selective amplification according to the invention is still achieved, involves the use of a template oligonucleotide modified within the target sequence to prevent copying back through the oligonucleotide upon amplification. Modifications that prevent copying include the insertion within the 3' region of the template oligonucleotide of one or more base analogues or one or more abasic sites, or any combination of these, that hinder or block copying of the oligonucleotide by the particular polymerase employed in the assay. As a result, extension products of the template oligonucleotide cannot be copied in a subsequent PCR cycle. For example, if Taq DNA polymerase is used in the amplification of DNA, the substitution of DNA nucleotides with RNA nucleotides such as 2-O-methyl RNA nucleotides will still allow hybridisation of the template oligonucleotide with target sequence. However, copying back through the template oligonucleotide will be blocked or inefficient due to the presence of the modified nucleotides. The incomplete copies will not participate in further amplification cycles. In order to allow thermocycling to proceed, a third oligonucleotide that shares sequence with the 5' tail of the template oligonucleotide is utilised, and thus only nucleic acid molecules having target sequence adjacent a 3'terminus, which is extended 3' complementary to the 5' tail, will be amplified.

Accordingly, a further aspect of the present invention provides a method for selective amplification from a sample of a nucleic acid molecule having a target sequence adjacent a 3' terminus in the presence of molecules comprising the target sequence not adjacent a 3' terminus but embedded within the molecule, the method comprising
  (i) contacting the sample with a template oligonucleotide having
    (a) a 3' region substantially complementary to the target sequence adjacent the 3' terminus a nucleic acid molecule;
    (b) a 5' tail comprising a nucleic acid sequence such that a free 5' tail is formed when the template oligonucleotide anneals to target sequence located adjacent a 3' terminus or embedded within a nucleic acid molecule, the 5' tail providing a template for extension of the 3' terminus of the target sequence incorporating sequence complementary to the 5' tail of the template oligonucleotide resulting in the addition of sequence complementary to the 5' tail to the target sequence; and
    (c) a modification in the 3' region that blocks 3' extension of said template oligonucleotide, or, a modification in the hybridizing region of the template oligonucleotide that permits 3' extension but hinders or blocks copying of said oligonucleotide in the 3' region of said oligonucleotide;
  (ii) contacting the sample with a second oligonucleotide for priming in a reverse direction to the template oligonucleotide;
  (iii) contacting the DNA sample with a third oligonucleotide sharing nucleotide sequence with the 5' tail of the template oligonucleotide and from which 3' extension proceeds unhindered; and
  (iv) carrying out amplification of the sample, wherein
    (a) annealing of the template oligonucleotide to nucleic acid molecules in the sample is followed by copying of the 5' tail of the template oligonucleotide when the template oligonucleotide anneals to target sequence adjacent a 3' terminus but not when the template oligonucleotide anneals to target sequence embedded within a nucleic acid molecule, in the presence of blocked 3' extension of the template oligonucleotide, or, in the presence of unhindered 3' extension of a template oligonucleotide from which subsequent copying is hindered or blocked; and
    (b) amplification proceeds with the second and third oligonucleotides, selectively amplifying target sequence located adjacent a 3' terminus by virtue of the copied 5' tail, amplification of target sequence embedded within a nucleic acid molecule not proceeding due to the absence of copying of the 5' tail and either blocked 3' extension of the template oligonucleotide, or blocked copying of the template oligonucleotide.

According to a further aspect, the present invention provides a method for selective amplification from a sample, of a nucleic acid molecule having a target sequence adjacent a 3' terminus, the terminus being the result of cleavage of the molecule, in the presence of uncleaved nucleic acid molecules comprising the target sequence embedded within the molecule, the method comprising:
  (i) contacting the DNA sample with a template oligonucleotide having
    (a) a 3' region substantially complementary to the target sequence adjacent the 3' terminus of a nucleic acid molecule;
    (b) a 5' tail comprising a nucleic acid sequence such that a free 5' tail is formed when the template oligonucleotide anneals to cleaved or uncleaved nucleic acid molecules, the 5' tail providing a template for extension of the 3' terminus of the target sequence incorporating sequence complementary to the 5' tail of the template oligonucleotide resulting in the addition of sequence complementary to the 5' tail to the target sequence; and
    (c) a 3' modification that blocks 3' extension of said template oligonucleotide; or, a modification in the hybridizing region of the template oligonucleotide that permits 3' extension but hinders or blocks copying of said oligonucleotide in the 3' region of said oligonucleotide;
  (ii) contacting the sample with a second oligonucleotide for priming in a reverse direction to the template oligonucleotide;
  (iii) contacting the sample with a third oligonucleotide sharing nucleotide sequence with the 5' tail of the template oligonucleotide and from which 3' extension proceeds unhindered; and
  (iv) carrying out amplification of the sample, wherein
    (a) annealing of the template oligonucleotide to target sequence adjacent a 3' terminus the result of cleavage of a nucleic acid molecule is followed by copying of the 5' tail of the template oligonucleotide but not when the template oligonucleotide anneals to target sequence embedded within an uncleaved nucleic acid molecule, in the presence of blocked 3' extension of said oligonucleotide, or, in the presence of unhindered 3' extension of a template oligonucleotide from which subsequent copying is hindered or blocked; and
    (b) amplification proceeds with the second and third oligonucleotides, selectively amplifying target sequence adjacent a 3' terminus by virtue of the copied 5' tail sequence, amplification of target sequence embedded within an uncleaved molecule not proceeding due to the absence of copying of the 5' tail and either blocked 3' extension of the template oligonucleotide, or blocked copying of the template oligonucleotide, resulting in selective amplification of cleaved nucleic acid molecules over uncleaved nucleic acid molecules.

According to a further aspect, the present invention provides a method for selective amplification from a sample of a nucleic acid molecule having a target sequence adjacent a 3' terminus, in the presence of a mixed population of molecules having differing 3' termini, the method comprising
  (i) contacting the sample with a template oligonucleotide having
    (a) a 3' region substantially complementary to the target sequence adjacent the 3' terminus;
    (b) a 5' tail comprising a nucleic acid sequence such that a free 5' tail is formed when the template oligonucleotide anneals to the target sequence adjacent a 3' terminus, the 5' tail providing a template for extension of the 3' terminus of the target sequence incorporating sequence complementary to the 5' tail of the template oligonucleotide resulting in the addition of sequence complementary to the 5' tail to the target sequence; and
    (c) a modification in the 3' region that blocks 3' extension of the template oligonucleotide, or, a modification in the hybridizing region of the template oligonucleotide that permits 3' extension but hinders or blocks copying of said oligonucleotide in the 3' region of said oligonucleotide;
(ii) contacting the sample with a second oligonucleotide for priming in a reverse direction to the template oligonucleotide;
(iii) contacting the DNA sample with a third oligonucleotide sharing nucleotide sequence with the 5' tail of the template oligonucleotide and from which 3' extension proceeds unhindered; and
(iv) carrying out amplification of the sample, wherein
   (a) specific annealing of the template oligonucleotide to target sequence is followed by copying of the 5' tail of the template oligonucleotide when the template oligonucleotide anneals to target sequence adjacent a 3' terminus but not when the template oligonucleotide anneals to non-complementary sequence adjacent a 3' terminus, in the presence of blocked 3' extension of the template oligonucleotide, or, in the presence of unhindered 3' extension of a template oligonucleotide from which subsequent copying is hindered or blocked; and
   (b) amplification proceeds with the second and third oligonucleotides selectively amplifying target sequence located adjacent a 3' terminus by virtue of the copied 5' tail sequence, amplification of non-complementary sequence adjacent a 3' terminus not proceeding due to the absence of copying of the 5' tail and either blocked 3' extension of the template oligonucleotide, or blocked copying of the template oligonucleotide, resulting selective amplification of target sequence adjacent a 3' terminus in the presence of a mixed population of 3' termini.

In one embodiment the nucleic acid molecules are DNA molecules.

The template oligonucleotide may include modified bases within its 3' region which when hybridized at the 3' terminus of a nucleic acid molecule will block 3' extension of that molecule.

Preferably, the 3' modification that blocks 3' extension of the template oligonucleotide includes the incorporation of one or more non-extendible moieties or nucleotide analogues at the 3' terminus, for example, a single 3' terminal non-extendible base or base analogue, a combination of a 3' terminal non-extendible base and nucleotide mismatches in the 3' region of the template oligonucleotide close to the 3' terminus, or the incorporation of abasic sites in the 3' region of the template oligonucleotide close to the 3'end. More preferably, the non-extendible base is selected from a 2', 3' dideoxynucleotide, a 3' C3, C18 or other length spacer, a 3' phosphorylated nucleotide, a "peptide nucleic acid" base, a "locked nucleic acid" (LNA) base, a nucleotide amine derivative, uracil treated with Uracil DNA glycosylase, RNA or a 2' O-Methyl RNA residue, or a combination of these.

It will be appreciated by the person skilled in the art that other methods of blocking extension may be suitable depending on the identity of the polymerase utilised. For example, a phosphorothioate base in combination with a nucleotide mismatch could be used to block extension in cases where a proofreading polymerase is desired to be used.

Preferably, the second oligonucleotide is either a further template oligonucleotide i.e. having features of the template oligonucleotide, or is a non-templating oligonucleotide, for example, consists of a single region of nucleotide sequence complementary to the extension product of the template oligonucleotide in the case where 3' extension of the template oligonucleotide is only delayed rather than blocked, or, consists of a single region of nucleotide sequence complementary to the extension product of the third oligonucleotide in the case where 3' extension of the template oligonucleotide is blocked.

In a preferred embodiment, the 3' terminus of a DNA molecule amplified by ES-PCR is the result of cleavage by sequence-specific restriction endonucleases. More preferably, the restriction endonucleases are sequence-specific methylation sensitive restriction enzymes, allowing for selective amplification, according to the methods of the invention, of unmethylated DNA over methylated DNA, or vice versa, depending on the use of restriction enzymes inhibited by DNA methylation, such as HpaII, HhaI, BstuI, NotI, SmaI and SacII, or restriction enzymes that selectively cut methylated DNA, such as GlaI, and BisI. In this manner, the methods of the invention allow for the detection of differences in methylation state between two DNA samples, providing an approach for the detection of diseased tissue where a change in methylation is associated with a diseased state. For example, changes in methylation state involving both demethylation of DNA, and hypermethylation of other specific DNA sequences are associated with the transformation of cells to the cancerous state. Accordingly, in a further aspect, the present invention provides a kit for the selective amplification of cleaved DNA from a DNA sample comprising cleaved and uncleaved DNA, the kit comprising (i) a template oligonucleotide, (ii) a second oligonucleotide, and (iii) a third oligonucleotide; according to the invention.

In a further preferred embodiment, the site of cleavage of DNA is selected to distinguish the presence or absence of a restriction site, thereby allowing for the detection of sequence differences between DNA samples, such as the detection of single nucleotide polymorphisms or mutations. Accordingly, the methods of the invention allow for genotyping for the purposes of genetic fingerprinting or the diagnosis of genetic disease associated with alterations in genomic sequence or detection of specific mutations that may be indicative of cancer cells.

The detection of instability in simple nucleotide repeats, including mononucleotide repeats, such as the deletion of one or more base pairs, may be achieved according to a further embodiment of the invention. The presence of a restriction enzyme recognition sequence near a mononucleotide repeat for a restriction enzyme which has a cleavage site at a defined distance outside its recognition sequence, herein referred to as a 'flanking cutter', can be utilised to distinguish the presence of deletion variants. If such a restriction site is not conveniently located near a mononucleotide repeat, it can be introduced, by a first round of PCR, for example. Where a deletion of base pairs has occurred between the cleavage site and the recognition sequence, the product of digestion of non-deleted repeat DNA will differ in nucleotide sequence adjacent the 3' terminus from the product of digestion of deleted repeat DNA. This is because the deletion of one or more base pairs will result in a shift in the 3' direction of the cleavage site, necessarily resulting in a change in sequence at the cleavage site. Thus, the design of template oligonucleotides that specifically anneal to deletion variants can be used to detect such variants.

For example, the template oligonucleotide may incorporate a length of complementary mononucleotide repeat that matches that of a DNA fragment resulting from digestion of a deletion variant in which at least one base pair has been deleted from the repeat sequence. The repeat sequence of the template oligonucleotide will allow annealing to a complementary repeat sequence adjacent the 3' terminus of a digestion fragment, but will only permit 3' extension of the digestion fragment of the deletion variant. This is because the fragment arising from non-deleted repeat DNA will necessarily have a nucleotide sequence distinct from that of the deletion variant, resulting in one or more mismatches between the template oligonucleotide and the 3' terminus of the digestion fragment, and thereby preventing 3' extension of the digestion fragment of the non-deleted repeat DNA. This design of the template oligonucleotide will not alter its ability to selectively amplify a target DNA located adjacent a 3' terminus over the same target sequence embedded within a DNA molecule, but demonstrates the added ability to distinguish between DNAs having certain 3' termini.

Whether the restriction site is located within a repeat sequence or downstream of the repeat sequence, a change in the length of a repeat sequence will result in a change in the site of restriction enzyme cleavage, resulting in a fragment having a different sequence to the fragment generated from repeat DNA that did not undergo a deletion.

The detection of instability in mononucleotide repeats such as the deletion of one or more repeats provides an approach for measuring microsatellite instability, as is noted to occur in the microsatellites of tumour cells. It would be clear to a person skilled in the art that this particular embodiment of the invention applies equally to the detection of instability in dinucleotide or other repeats such as, trinucleotide and tetranucleotide repeats where a restriction enzyme recognition site is appropriately located (or introduced) as described.

Embodiments of the invention that utilise flanking cutters may also be applied to detection of an insertion of base pairs in a nucleic acid molecule.

Where a nucleic acid variant results from the insertion of base pairs, a shift in the cleavage site in the 5' direction will occur, thereby resulting in a different sequence adjacent the 3' terminus resulting from cleavage than if no insertion existed. It would be apparent to a person skilled in the art that the use of flanking cutters could be applied to the detection of a deletion or insertion in any nucleic acid molecule, and that the application of flanking cutters is not limited to detecting deletions in mononucleotide repeat sequences but equally applies to any nucleic acid molecule variant resulting from of a deletion or insertion of one or more base pairs.

Accordingly, a further aspect of the invention provides a method for detecting the presence or absence of a deletion or insertion in a nucleic acid molecule in a sample wherein the deletion or insertion occurs between a restriction enzyme recognition site and its cleavage site located outside the recognition site at a defined distance, the method comprising
  (i) digesting the sample with the restriction enzyme having a cleavage site outside its recognition site at a defined distance, and
  (ii) determining the nucleotide sequence adjacent a 3' terminus generated by cleavage wherein the nucleotide sequence adjacent the 3' terminus will depend on the presence or absence of a deletion or insertion, and wherein a shift in the cleavage site either in the 3' or 5' direction will occur in the presence of a deletion or insertion, respectively.

Determination of the nucleotide sequence adjacent a 3' terminus resulting from cleavage by a flanking cutter can be achieved by ES-PCR, or by other selective amplification approaches.

In a further embodiment, methods of the invention may be utilised for the detection and quantitation of RNA transcript variants. mRNA copied to cDNA will comprise a population of cDNAs having a range of 3' termini according to their corresponding 5' mRNA sequence. Where exon sequences are known, template oligonucleotides can be prepared that will distinguish between alternatively spliced mRNAs, according to the sequence identity of the first exon.

The 5' tail of the template oligonucleotide according to the present invention provides a template for extension of the 3' terminus of the target sequence only when the template oligonucleotide anneals to nucleic acid molecules having target sequence adjacent a 3' terminus. Extension of the 3' terminus of the target sequence complementary to the 5' tail of the template oligonucleotide results in the addition of sequence complementary to the 5' tail to the target sequence. Thus, following reaction conditions that allow annealing of the template oligonucleotide to target sequence and 3' extension of the target sequence complementary to the 5' tail of the template oligonucleotide, nucleic acid molecules in the sample originally having target sequence adjacent a 3' terminus now also include further sequence 5' of the target sequence that is complementary to the 5' tail of the template oligonucleotide. This sequence complementary to the 5' tail can be utilised to detect those molecules that originated in the sample as having target sequence adjacent a 3' terminus.

Accordingly, a further aspect of the invention provides a method for detecting in a sample a nucleic acid molecule having a target sequence adjacent a 3' terminus, the method comprising:
  (i) contacting the sample with a template oligonucleotide having
    (a) a 3' region substantially complementary to the target sequence adjacent the 3' terminus of a nucleic acid molecule,
    (b) a 5' tail comprising a nucleic acid sequence such that a free 5' tail is formed when the template oligonucleotide anneals to the target sequence located adjacent a 3' terminus, the 5' tail providing a template for extension of the 3' terminus of the target sequence incorporating sequence complementary to the 5' tail of the template oligonucleotide resulting in the addition of sequence complementary to the 5' tail to the target sequence, and
    (c) a modification in the 3' region that delays 3' extension of said template oligonucleotide;
  (ii) providing reaction conditions to allow annealing of the template oligonucleotide to the sample, wherein annealing of the template oligonucleotide to target sequence adjacent a 3' terminus allows for subsequent 3' extension of the target sequence complementary to the 5' tail;
  (iii) providing reaction conditions to allow 3' extension of the target sequence complementary to the 5' tail, in the presence of delayed or blocked 3' extension of said oligonucleotide; and
  (iv) detecting nucleic acid molecules having target sequence adjacent a 3' terminus by
    (1) detecting the nucleic acid sequence complementary to the 5' tail of the template oligonucleotide resulting from 3' extension of the target sequence adjacent a 3' terminus; or
    (2) utilising the nucleic acid sequence complementary to the 5' tail of the template oligonucleotide resulting from 3' extension of the target sequence adjacent a 3' terminus, to copy the nucleic acid molecule having a target sequence adjacent a 3' terminus.

The detection of nucleic acid sequence complementary to the 5' tail of the template oligonucleotide may be achieved through any known means of detecting a nucleic acid molecule of known sequence, for example, by direct labelling of the 3' extension reaction of the target sequence complementary to the 5' tail with a radiolabeled or fluorescently labeled nucleoside triphosphate such as $\alpha^{32}$P-dCTP or Cy5-dCTP or a biotinylated nucleoside triphosphate, or capture of the incorporated complementary sequence with a sequence specific probe through hybridisation, or through direct capture of the nucleic acid sequence complementary to the 5' tail of the template oligonucleotide.

The nucleic acid sequence complementary to the 5' tail of the template oligonucleotide may be utilised in copying nucleic acid molecules having a target sequence adjacent a 3' terminus by a variety of means. For example a primer complementary to the incorporated sequence can be used to prime synthesis that will extend back through the target sequence. Alternatively the 5' tail of the template oligonucleotide may provide a promoter and start site for a polymerase such as T7 RNA polymerase such that the addition of sequence complementary to the 5' tail provides a template for copying through the target sequence by the polymerase. Copied nucleic acid molecules having target sequence adjacent a 3' terminus can be detected by any known means of detecting a nucleic acid molecule of known sequence, such as the approaches cited above including hybridisation and PCR.

It would be abundantly clear to a person skilled in the art that cDNA copied from RNA is a suitable nucleic acid for the purposes of the present invention.

Throughout this specification, unless the context requires otherwise, the words "comprise," "comprises" and "comprising" will be understood to imply the inclusion of a stated step or element or group of steps or elements but not the exclusion of any other step or element or group of steps or elements.

The articles "a" and "an" are used herein to refer to one or to more than one (i.e. to at least one) of the grammatical object of the article. By way of example, "an element" means one element or more than one element.

BRIEF DESCRIPTION OF THE FIGURES

FIG. 2: Primer sites for 21qTFMLHC/T and 21qTRC on BstIU-cleaved DNA and uncleaved DNA (tandem repeat sequence on human chromosome 21 in band 21q22.3.), corresponding end-specific oligonucleotide primer having a 3' terminal nucleotide mismatch, and a second oligonucleotide primer for priming in the reverse direction, according to an embodiment of the present invention.

FIG. 4A: Primer sites for forward primer 21qTFMLHC/T and reverse primer 21qTRM13, both end-specific template oligonucleotides, in a tandem repeat sequence on human chromosome 21 in band 21q22.3.

FIG. 5A: Primer sites for MycRM1, an end-specific template oligonucleotide having a 3' terminal nucleotide mismatch and reverse primer MycFC1, within the Myc gene targeted at a HpaII site found to be hypomethylated in colorectal cancer (Sharrard et al. 1992).

FIG. 5B: Table of Ct values and amplification curves showing detection of hypomethylated myc DNA in K562 DNA compared to the fully-methylated DNA of CpGenome™; and the detection of reduced methylation at the HpaII site in colorectal tumour tissue 35/03 as compared to its matched normal sample 34/03.

FIG. 6A: Primer sites for targeting the 5'(promoter) region of LINE retrotransposable element, corresponding insertion template oligonucleotides acting as forward and reverse amplification primers, and the nucleotide sequence of the HEX-labelled LPAHex probe.

FIG. 6B; Amplification curves and Tables showing Ct values for amplification from substantially hypomethylated K562 DNA or from fully methylated DNA, as detected with either SYBR Green or the HEX-labelled probe.

FIG. 7A: Primer sites for targeting the first BstUI site in the consensus sequence of Alu elements with a template oligonucleotide blocked from 3' extension by a phosphate group, and corresponding second oligonucleotide primer for priming in the reverse direction, and JOELUX primer for priming in the forward direction, according to an embodiment of the present invention.

FIG. 8A: Primer sites for targeting methylated DNA through a GlaI site within the CpG island of the hMLH1 gene. The template oligonucleotide incorporates 3 mismatches at its 3' end, two of which are converted to abasic sites when digested by uracil DNA glycosylase, corresponding MLHRev3 reverse primer, and forward LUX primer, according to an embodiment of the present invention.

FIG. 9A: Detection of a point mutation in the BRAF gene. First round PCR primer BRFMX used to introduce an XbaI restriction site dependent on the presence of the T to A transversion at the mutation site (underlined within target sequence).

FIG. 9B: Detection of a point mutation in the BRAF gene. ES-PCR primer BRFU used in combination with an outer overlapping JOELUX primer and a reverse primer BRF2.

FIG. 10A(i): Products of restriction enzyme cleavage in a mononucleotide repeat adjacent to a Bbr7I restriction site.

FIG. 10A(ii) and 10A(iii): Products of extension of the bottom strand of cut molecules using terminal transferase and primer annealing to the extended products.

FIG. 10A(iv): Template oligonucleotide for ES-PCR annealing to the cut bottom strand from the short and long molecules shown in FIG. 10A(i).

FIG. 10B(i): Molecules with repeats of nine or ten As adjacent to an MmeI restriction site.

FIG. 10B(ii): Products of cleavage of the molecules of FIG. 10B(i) with MmeI

FIG. 10B(iii): Linker ligation showing specific ligation to cut ends of the molecule of FIG. 10B(ii) originating from the molecule with nine As (Fig.10B(i)).

FIG. 10B(iv): Template oligonucleotide for ES-PCR annealing to the cut bottom strand from the "nine" and "ten" molecules.

FIG. 10C: This figure depicts the polynucleotide sequences of SEQ ID NOs:84, 85 and 86.

FIG. 11A(i): The NR22 microsatellite region showing the location of an MboII site and reverse primer sequence.

FIG. 11A(ii) and 11A(iii): Sequences of two template oligonucleotides F1NR22-0 and J5NR22-4 for amplification of mononucleotide repeats of different lengths in the NR22 microsatellite following digestion with MboII.

FIGS. 11B(i) and 11B(ii): Amplification curves showing results of amplification of blood DNA and DNA from HCT116 cells that carry deletions within the NR-22 microsatellite.

FIG. 12B: Oligonucleotides utilized in ES-PCR selective amplification of an insertion mutation of 1 bp or 4 bp. The template oligonucleotide employs 2' O-Methyl nucleotides to block 3' extension from the 3' terminus of cleaved target DNA.

FIG. 12C: Amplification curves showing selective amplification of DNA including a 1 bp or 4 bp insertion over DNA having no insertion, i.e. "Normal" DNA.

FIGS. 13A and 13B: Sequence of test DNAs representative of "uncut" and "cut" DNA, a reference template oligonucleotide AluPhB blocked for extension by a phosphate at its 3' terminus and second and third oligonucleotides, utilized in a series of ES-PCR experiments to assess the effect on ES-PCR of modifications in template oligonucleotide (FIG. 13B).

FIG. 13C: Amplification curves showing results of ES-PCR when using the various template oligonucleotides given in FIG. 13B.

DEFINITIONS

Figure 1:
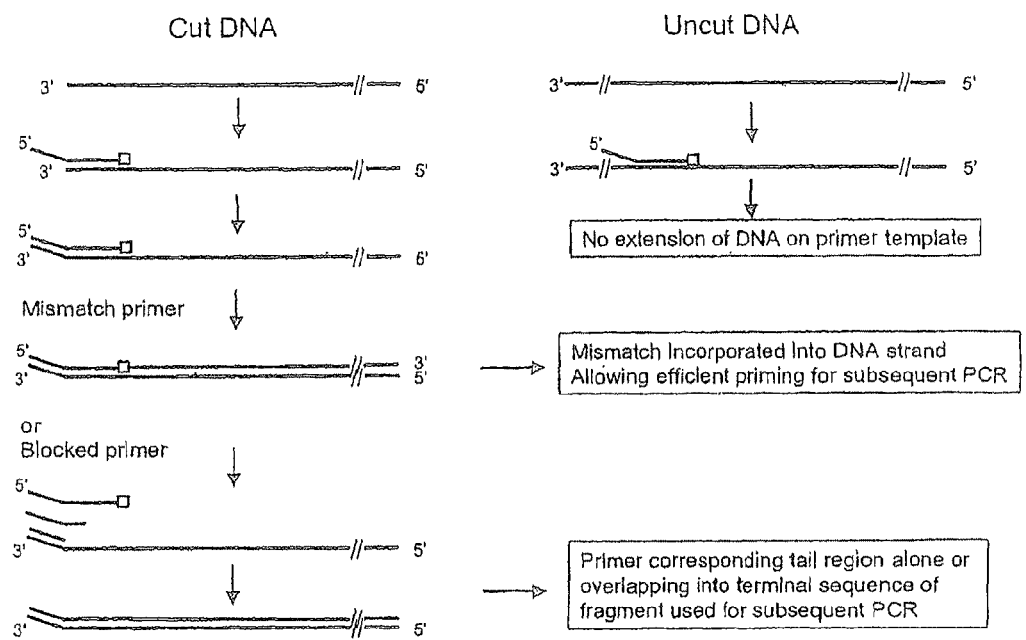
FIG. 1: Schematic outlining the principle of end-specific PCR to selectively amplify cleaved DNA over uncleaved DNA.

When used in the context of the present invention, the term "sample" refers to any biological sample that comprises nucleic acid molecules, typically comprising DNA and/or RNA. Samples may be tissues, cells or extracts thereof, or may be purified samples of nucleic acid molecules. Use of the term "sample" does not imply the presence of target sequence either adjacent a 3' terminus of a nucleic acid molecule or embedded within a nucleic acid molecule. The presence in a sample of target sequence embedded within a nucleic acid molecule is not required for selective amplification of target sequence adjacent a 3' terminus. Thus, the template oligonucleotide will serve to amplify a nucleic acid molecule having target sequence adjacent a 3' terminus regardless of whether or not the target sequence is also present in the sample, located embedded within a nucleic acid molecule.

When used in the context of the present invention, the term "target sequence" refers to a nucleic acid sequence to which the template oligonucleotide of the present invention anneals with specificity by virtue of the template oligonucleotide having nucleotide sequence at its 3' region substantially complementary to the target sequence. When located adjacent a 3' terminus the target sequence is representative of nucleic acid molecules selectively amplified by ES-PCR.

As used in the context of the present invention, the term "adjacent a 3' terminus" refers to the region of nucleotides immediately 5' of the 3' terminus and extending 5' of the 3' terminus of a nucleic acid molecule, typically including the terminal nucleotide. The region "adjacent a 3' terminus" beginning from the terminal nucleotide of a nucleic acid molecule having a 3' terminus, corresponds in length to the 3' region of the template oligonucleotide complementary to the target sequence.

As used in the context of the present invention, the phrase "embedded within a nucleic acid molecule" refers to a location not adjacent a 3' terminus as defined above, but displaced from a 3' terminus by a least one nucleotide 5' of the 3' terminus. Thus, the target sequence embedded within a nucleic acid molecule may be located within a nucleic acid molecule the distance of one or more nucleotides from the 3' terminus.

When used in the context of the present invention, the term "targeted molecule" or "targeted nucleic acid molecule" refers to a nucleic acid molecule having a target sequence located adjacent a 3' terminus resulting in its selective amplification by methods of the invention.

When used in the context of the present invention, the term "cleaved nucleic acid molecule" is intended to refer to a molecule that has been digested by restriction endonucleases or any other enzymes that generate nucleic acids with 3' termini, and encompasses DNA digested by restriction endonucleases or other enzymes generating 3' termini.

When used in the context of the present invention, the term "template oligonucleotide" or "templating oligonucleotide" refers to a nucleic acid oligonucleotide that comprises a 5' region that forms a 5' tail when its 3' region anneals to nucleic acid and that allows 3' extension of a target sequence to which it anneals when located adjacent a 3' terminus of a nucleic acid molecule. In certain embodiments of the invention, the template oligonucleotide is incorporated into PCR amplicons because 3' extension of the oligonucleotide takes place. In such cases, the template oligonucleotide serves as a forward primer.

In other embodiments, the template oligonucleotide is not incorporated into PCR amplicons because 3' extension of the oligonucleotide is blocked, or because copying of the 3' region of the oligonucleotide is blocked. In these settings, an additional 'third' oligonucleotide sharing sequence with the 5' tail of the template oligonucleotide is used as a forward primer.

The template oligonucleotides of the invention may comprise non-DNA nucleotides, such as RNA nucleotides, nucleotide analogues, or other non-nucleic acid molecules that can be incorporated into the oligonucleotide in order to delay or block 3' extension, or to block copying from the oligonucleotide. A person skilled in the art will appreciate that any means of delaying 3' extension or blocking 3' extension or copying of the oligonucleotide can be applied to a template oligonucleotide according to the present invention, provided that the chosen means does not prevent 3' extension of the target sequence.

When used in the context of the present invention, the term "substantially complementary" refers to complementarity between nucleic acids such that adequate hybridisation occurs to achieve selective amplification of a nucleic acid molecule having target sequence adjacent a 3' terminus over target sequence embedded within a nucleic acid molecule, according to the present invention. Thus, not all bases in an oligonucleotide need be complementary to the region of a molecule to which it will hybridise; the oligonucleotide need only contain sufficient complementary bases to enable the oligonucleotide to recognize and hybridise with it's 'target' molecule. Thus the term "substantially complementary" encompasses nucleic acids that incorporate one or more mismatches, deletions, insertions, combinations of deletions and insertions, or any other sequence modification that does not abolish annealing of nucleic acids with specificity.

As used in the context of the present invention, the term "delayed 3' extension" refers to 3' extension of the template oligonucleotide that is hindered from proceeding, but not blocked, so that 3' extension of the oligonucleotide occurs less efficiently than if the modification to delay 3' extension were absent. Thus, in this setting the template oligonucleotide will act as a forward primer in the amplification reaction.

As used in the context of the present invention, the term "blocked 3' extension" refers to the absence in practical terms of 3' extension of the template oligonucleotide, such that the amplification reaction will not proceed, or proceeds at an unworkable rate, unless an additional 'third' oligonucleotide is added to the reaction, this oligonucleotide sharing sequence with the 5' tail of the template oligonucleotide and from which 3' extension will occur.

As used in the context of the present invention, the term "amplification" refers to making one or more copies of the targeted molecule, and includes, but is not limited to the amplification of nucleic acid molecules by the polymerase chain reaction (PCR). PCR may refer to linear, non-exponential amplification of DNA in addition to exponential amplification of DNA, where the person skilled in the art would recognize that either form of amplification is appropriate for the purpose of the invention.

As used in the context of the present invention, the term "flanking cutter" refers to a restriction endonuclease that cleaves nucleic acid at a defined distance from its recognition sequence.

DETAILED DESCRIPTION OF THE INVENTION

The principle of end-specific PCR or ES-PCR as embodied by the present invention is shown in FIG. 1. ES-PCR depends upon the use of at least one oligonucleotide, herein referred to as the template oligonucleotide, that is in some way partially or completely blocked from extension. The template oligonucleotide is designed to overlap the 3' terminus of a nucleic acid molecule generated, for example, by restriction digestion. The 3' portion of the template oligonucleotide substantially matches the specific sequence adjacent the cleaved end of the nucleic acid molecule while the 5' portion contains nucleic acid sequence that forms a tail upon annealing of the template oligonucleotide to nucleic acid molecule.

Upon annealing of the template oligonucleotide to a cleaved nucleic acid molecule, elongation of the template oligonucleotide is delayed or blocked, but the 3' terminus of the targeted molecule is able to be extended to allow copying of the 5' tail of the template oligonucleotide.

Target sequence that is embedded within a nucleic acid molecule, because for example it has not been cleaved by a restriction enzyme at a desired restriction site, can anneal with the template oligonucleotide however 3' extension of the target sequence to allow copying of the 5' tail of the template oligonucleotide cannot occur due to the absence of a 3' terminus at the site of annealing. Importantly, the nucleotide sequence added to the target sequence by extension of the free 3' terminus complementary to the 5' tail of the template oligonucleotide is subsequently used in the amplification of the targeted nucleic acid molecule. The added sequence also allows for modifications of ES-PCR, for example, the incorporation of a tag such as a biotinylated nucleotide that could be used to selectively capture molecules containing extended 3' sequences. Use of two different template oligonucleotide types is demonstrated, however, it would be clear to a person skilled in the art that any design feature incorporated at the 3' end of the template oligonucleotide resulting in delayed or blocked extension could be used to achieve the methods of the invention.

Typically the nucleic acid molecules to be analysed in accordance with the invention comprise DNA. However those skilled in the art will readily appreciate that methods of the present invention are also applicable to other nucleic acid molecules, such as RNAs, with the provision of the appropriate reagents, for example, RNA polymerases or reverse transcriptases, appropriate for amplification or copying of RNA. It will also be readily appreciated that the incorporated tail formed by copying of the 5' region of the template oligonucleotide may be detected directly or used to copy the target nucleic acid sequence by other means than thermocycling.

In one embodiment, the template oligonucleotide is able to anneal weakly to the target sequence, but is designed such that 3' extension from the template oligonucleotide is poor because of a deliberate mismatch with the target sequence at its 3' end. If the template oligonucleotide anneals to the target sequence adjacent a 3' terminus, however, the nucleic acid, for example, genomic DNA, can be extended 3' using the template oligonucleotide as template. The subsequent increased length of the hybridizing region between the template oligonucleotide and targeted nucleic acid molecule stabilises hybridisation of the template oligonucleotide and greatly enhances the efficiency with which it now primes and extends on the target nucleic acid molecule. Once the mismatched template oligonucleotide is incorporated into the amplicon, PCR continues efficiently, as the originally mismatched template oligonucleotide now fully matches its target sequence. In one example, priming on uncleaved DNA is limited through the combination of a short 3' region of the of template oligonucleotide and a terminal mismatch on the template oligonucleotide. As well as a terminal mismatch, other means can be used to limit priming from the template oligonucleotide.

In an embodiment of the invention utilizing a terminal mismatch, extension is inefficient unless copying of the 5' tail of the template oligonucleotide has occurred. Any other modifications that reduce or delay extension of a template oligonucleotide could be used to achieve ES-PCR, eg incorporation of a deliberate short deletion or insertion in the template oligonucleotide.

In a further embodiment of the invention, the template oligonucleotide can terminate at its 3' end with a non-extendible base, or can include modifications that will prevent 3' extension. In the case of completely end-blocked ES-PCR oligonucleotides, an additional third oligonucleotide is needed in the reaction to allow for eventual extension of the targeted nucleic acid molecule. The additional third oligonucleotide may consist of the nucleic acid sequence of the 5' tail of the template oligonucleotide or may overlap with the target sequence to include some target-specific sequence. If the third oligonucleotide primer used for amplification consists only of sequence of the 5' tail of the template oligonucleotide, it is possible to multiplex amplification of different nucleic acid molecules using a set of template oligonucleotides that are gene or fragment-specific but contain a common extension. In this embodiment any means of blocking extension can be used, including, but not limited to a C3 spacer, termination with a dideoxynucleotide, phosphorylation, the use of amine, abasic sites, uracil (combined with incubation with uracil DNA Glycosylase) and/or 2' O-methyl RNA residues. In the case of using DNA analogues that cannot be copied by DNA polymerases, ES-PCR can be achieved despite 3' extension of the template oligonucleotide. Combinations of blocked and mismatch template oligonucleotides are also possible variations that can be used in accordance with the present invention.

The template oligonucleotide may include modified bases within its 3' region which when hybridized at the 3' terminus of a nucleic acid molecule will block 3' extension of that molecule. This allows for selective amplification of target DNA having a target sequence adjacent its 3' terminus that does not hybridise at its 3' terminus with the modified bases of the template oligonucleotide, thereby not being blocked for 3' extension.

The template oligonucleotide may comprise nucleotide sequence complementary to target sequence that spans more than one possible location at which hybridization of a 3' terminus of nucleic acid molecule may occur. Thus, depending on the location of hybridization of a 3' terminus on the template oligonucleotide, the resulting 5' tail of the template oligonucleotide may or may not include sequence complementary to targeted nucleic acid molecule. Modified bases blocking 3' extension from the 3' terminus of a hybridised nucleic acid molecule may be positioned in the template oligonucleotide at one or more of the possible locations for 3' terminus hybridization representative of hybridization of 3' termini of non-targeted nucleic acid molecules, such that 3' extension of a nucleic acid molecule occurs only from the location of hybridization distinctive for the 3' terminus of the targeted nucleic acid molecule.

As with other amplification methods, conditions such as annealing times, extension times, and temperatures are dependent on specific sequences and require individual optimization. The inventors have found two or more stages useful in PCR reaction to allow greater flexibility in the design of ES-PCR. In general, lower hybridisation temperatures and longer incubation times are typically used in the first stage because priming of the target on the usually short (low Tm) part of the template oligonucleotide is expected to be relatively inefficient. In the case of mismatched and insertion/deletion template oligonucleotides, a prolonged incubation period is typically used in the first stage to allow eventual extension after binding has been stabilized by the 3' extension of the target sequence. After the initial 5 cycles it is expected that the PCR is being driven largely by oligonucleotides that match their target along their entire length and so a higher temperature (and usually shorter incubation times) can be employed in the second stage. Shorter denaturation times (and in some cases lower temperatures—not shown in these examples) can be employed in the second stage because the PCR product that now dominates the reaction is much more easily denatured than the various DNA molecules expected to be important during the first stage. Shorter denaturation times are advantageous in that there will be less inactivation of Taq DNA Polymerase.

However, the use of two stages is not a requirement for ES-PCR. By the use of longer complementary regions in the template oligonucleotide(s), particularly for the fully blocked template primers, a one-stage PCR can be developed.

Restriction enzyme digestion of sample may be carried out in a separate reaction prior to ES-PCR, or may be carried out in a single digestion-amplification reaction mix immediately prior to PCR.

As with other methods in which a common sequence is added to the ends of DNAs to be amplified (Elnifro, E M et al. 2000; Wittwer, C T et al. 2001) ES-PCR can be readily adapted for multiplex PCR.

ES-PCR products may be detected by standard methods well known to those skilled in the art including, but not limited to, including gel electrophoresis, realtime monitoring using non-specific DNA binding dyes such as SYBRGreen, sequence specific fluorescent probes or hybridisation to arrays.

In order that the invention may be readily understood and put into practical effect, particular preferred embodiments will now be described by way of the following non-limiting examples.

EXAMPLE 1

Use of a Single Mismatched Template Oligonucleotide to Select for Cleaved DNA

The region targeted is a tandem repeat (consensus size of 74 base pairs, GCGTGGCTGTCTCCACTGAGTCCCGG-GCACGGGTCAGGCTAACCGCGGGAGGAAATTTAATC-TAGAGTTTAACTT (SEQ ID NO: 1) present on Human chromosome 21 in band 21q22.3. In the Human genome (May 2004 assembly) the genomic size of the repeated region is 2218 base pairs, chr21:46536826-46539043. The restriction enzyme BstuI was used to cut genomic DNA at the underlined CGCG site. Cutting by BstUI is blocked by cytosine methylation so restriction ends will be formed only from unmethylated DNA.

In this example the template oligonucleotide also acts as the 'Forward' primer and has a 3' terminal mismatch with the target, genomic DNA. The sequence and primers used are shown in FIG. 2. The forward, mismatch primer and template oligonucleotide is 21qTFMLHC/T, 5' CACTCCCACTCGG-GAGGAATTTAATCTAGC 3' (SEQ ID NO:2) and the reverse, completely matched primer is 21qTRC, 5' ACCCGT-GCCCGGGACTCA 3' (SEQ ID NO:3). Underlined bases are the ones that do not match the initial target sequence.

PCRs were carried out in 25 microlitres of 20 mM Tris-HCl (pH 8.4), 50 mM KCl, 2.7 mM $MgCl_2$, 0.2 mM dCTP, 0.2 mM dGTP, 0.2 mM dATP, 0.4 mM dUTP, 200 nM primers, 1/125,000 dilution of SYBR® Green I (Molecular Probes Cat. No. S7563) 20 nM fluorescein calibration dye (BioRad) 1 unit of BstUI (New England Biolabs) and 0.5 units of Platinum Taq Polymerase (Invitrogen). A Corbett RotorGene 3000 was set to run at 60 C for 5 minutes, 95 C for 2 minutes then 5 cycles of 95 C 15 seconds-65 C 3 minutes, and then 40 cycles of 95 C 5 seconds-65 C 30 seconds. BstUI digestion occurs during the initial 5 min incubation at 60 C. The longer extension time in the first 5 cycles is to allow for extension of the target DNA under conditions where target/primer annealing is unstable.

The fluorescein is present because reactions were sometimes run in a BioRad Icycler, and this machine requires a trace of fluorescein (or some other dye) for calibration purposes. This low level is not expected to have any significant effect on the results.

Figure 3A:
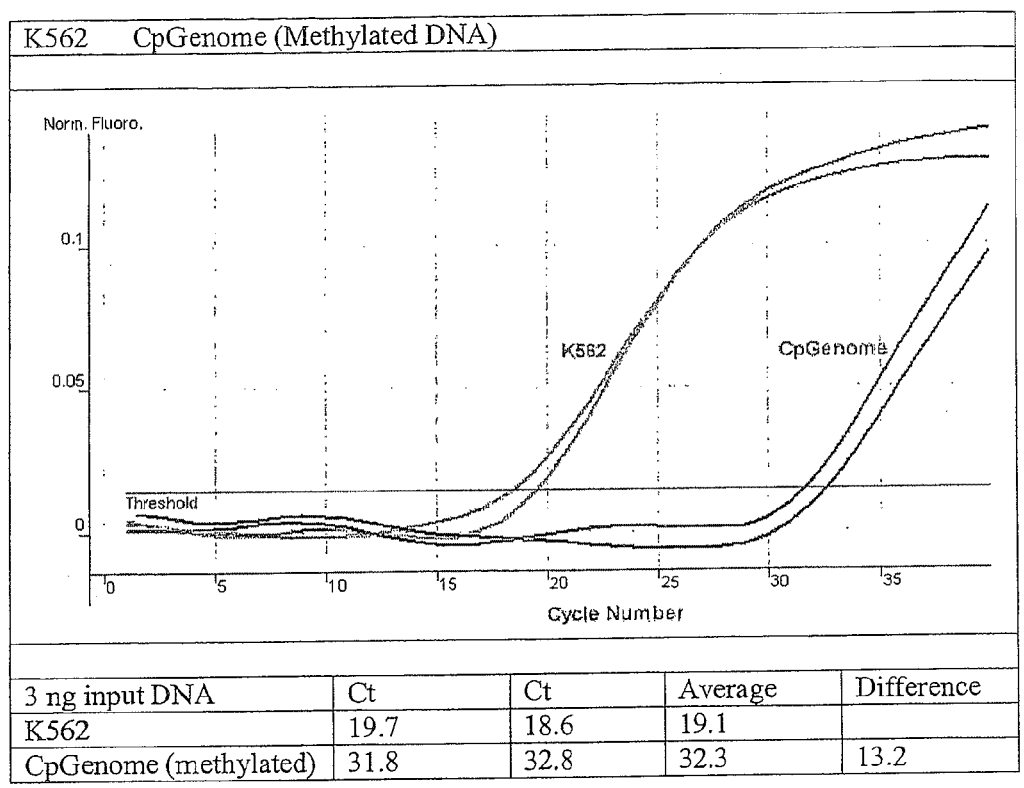
FIG. 3: Amplification curves and Tables showing Ct values for (i) fully methylated DNA (CpGenome™, Chemicon International, Inc.) and K562 hypomethylated DNA; (ii) DNA from matched normal and colorectal tumour tissue samples 29/99 and 30/99, respectively; (iii) matched normal and colorectal tumour tissue samples 34/03 and 35/03, respectively.
Figure 3B:
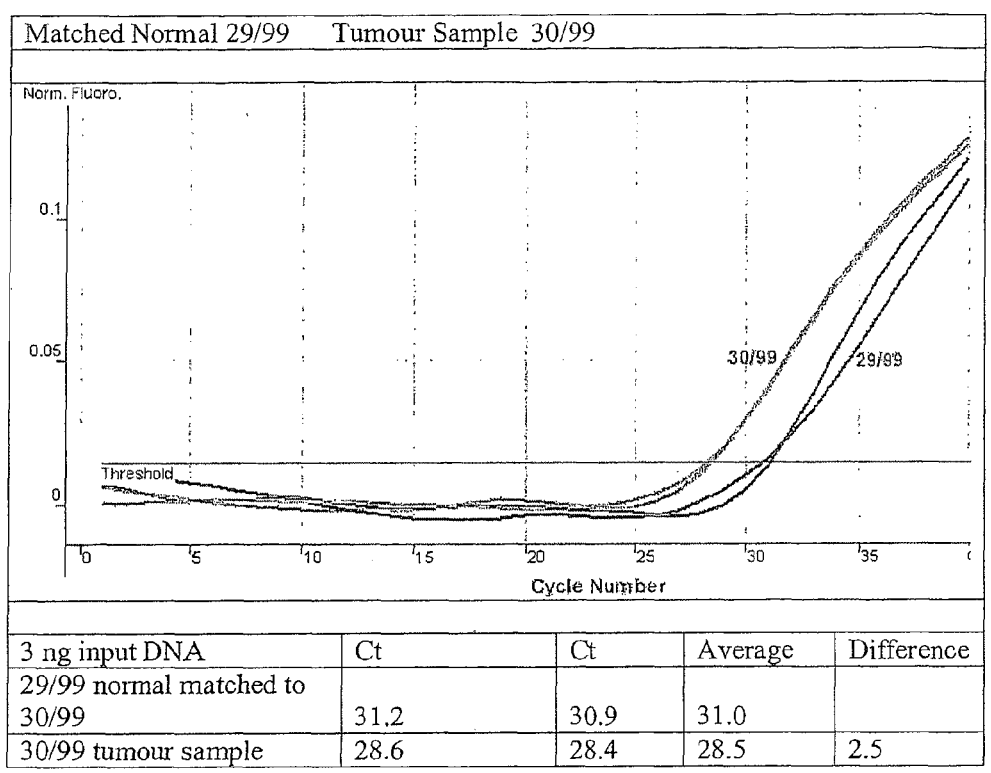
Figure 3C:
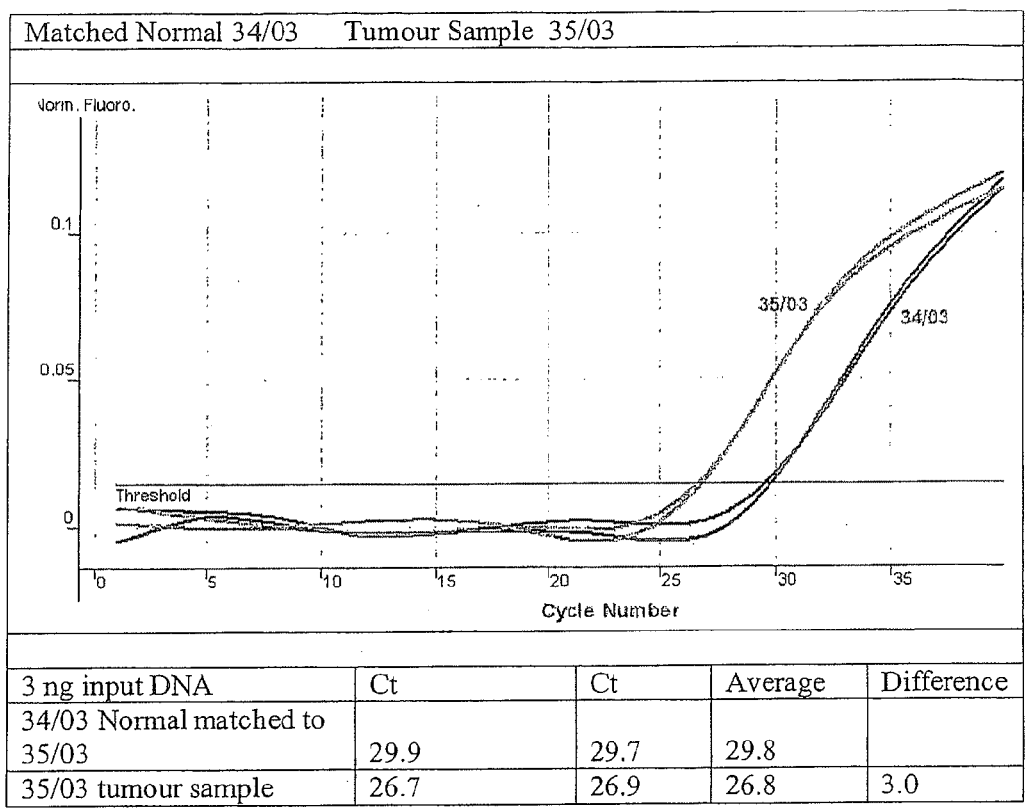

DNAs used for amplification were CpGenome DNA (Chemicon) that was enzymatically methylated at all CpG sites and DNA from the human chronic myelogenous leukemia cell line K562 as well as DNA from two pairs of matched colorectal tumour and adjacent normal colon DNA. The first panel of FIG. 3 shows the amplification curves for fully methylated DNA and for K562 DNA that is substantially hypomethylated at many repeat sequences. Amplification is highly selective for unmethylated DNA with K562 amplifying about 13 cycles ahead of fully methylated CpGenome DNA. Two examples are shown in panels B and C of colorectal cancer DNA and DNA isolated from adjacent normal tissue. In both cases the earlier amplification of the cancer DNA (by 2.5 to 3 cycles) is indicative of hypomethylation relative to the normal tissue.

EXAMPLE 2

Both Forward and Reverse Oligonucleotides are Template Oligonucleotides Having a 3' Terminal Mismatch The same repeat sequence from Chromosome 21q was amplified using both forward and reverse mismatch template oligonucleotides as primers. PCR conditions were the same as for Example 1 except that the probe 21qTRHEX 5' HEX-CCGTGCCCGGGACTCAGTGG BH1 (SEQ ID NO:4; From Sigma) was included at 100 nM and the reverse primer was 21qTRM13, 5' CCCTCACACTCGGTTAGCCTGACT 3' (SEQ ID NO:5). Underlined bases are the ones that do not match the initial target sequence.

Real time PCR was carried out using a Corbett RotorGene 3000 with the program: 60 C for 5 minutes, 95 C for 2 minutes then 3 cycles of 95 C 15 seconds-65 C 3 minutes, and then 60 cycles of 95 C 5 seconds-65 C 15 seconds. 3 ng/uL human genomic DNA containing different proportions of K562 DNA (known to have reduced levels of CpG methylation) and CpGenome DNA (artificially methylated DNA) were made by making dilutions in TEX (10 mM Tris HCl pH8, 0.1 mM EDTA, 0.01% Triton X100). 1 uL of the DNA mix was added to each 25 uL reaction.

Figure 4B:
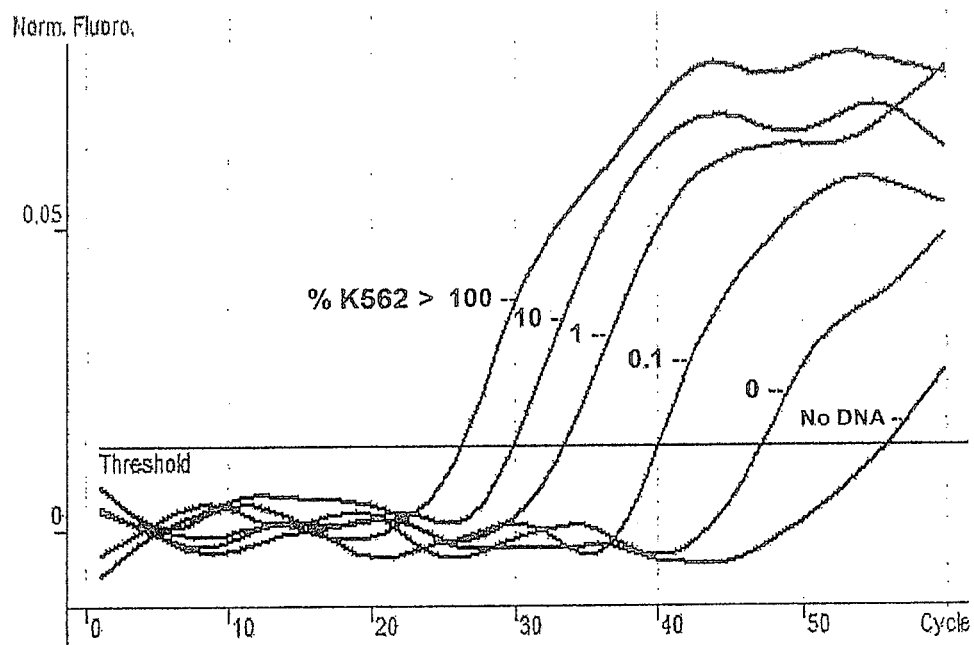
FIG. 4B: Table showing Ct values and SYBR Green amplification curves showing detection of hypomethylated K562 DNA well ahead of fully methylated DNA. A level of 0.1% K562 DNA sample, a single genome equivalent) is clearly detected 7 cycles before the sample containing only fully methylated DNA.

The SYBR Green results are shown in FIG. 4. In this experiment the extra specificity afforded by using a specific probe gave no advantage and the results were similar to the SYBR Green results and thus are not shown.

Amplification from the K562 DNA is detected more than 20 cycles ahead of fully methylated DNA and a level of 0.1% K562 DNA sample (3 pg, a single genome equivalent) is clearly detected 7 cycles before the sample containing only fully methylated DNA.

EXAMPLE 3

Targeting of a HpaII Site within C-Myc—Single Copy Gene

A HpaII site (underlined) within the c-myc gene sequence GAGCGCCAGAGGAGGAACGAGCTAAAACGGAGCT-TTTTTGCCCTGCGTGACCAGATCCCGGAGTTGGAA-AA (SEQ ID NO:6), chr8:128,822,153-128,822,223 in the human genome HG17 Build is targeted in this example. The HpaII site was found to be hypomethylated in colorectal cancer by Sharrard et al 1992. The sequence of the region and the template oligonucleotide (MycRM1) and primer MycFC1 are shown in FIG. 5A.

The DNA samples were cut with HpaII in a separate reaction. Digests were carried out for 2 hours at 37 C in New England Biolabs Buffer 1 (10 mM Bis Tris Propane-HCl, 10 mM MgCl$_2$, 1 mM DTT (pH 7.0 at 25° C.))+100 ug/ml BSA. 30 nanograms of DNA was cut with 5 units of HpaII in a volume of 30 uL. After a 20 minute heat treatment at 70 C, 24 uL of TEX (10 mM Tris pH7.4, 0.1 mM EDTA, 0.01% Triton X100) and 6 uL 50 mM EDTA was added giving equal final concentrations of magnesium ion and EDTA, and 0.5 ng/uL final DNA concentration. 2 uL of these samples were used for each PCR.

PCRs were carried out in 25 microlitres of 20 mM Tris-HCl (pH 8.4), 50 mM KCl, 2.7 mM MgCl$_2$, 0.2% glycerol, 0.2 mM dCTP, 0.2 mM dGTP, 0.2 mM dATP, 0.4 mM dUTP, 200 nM primers, 1/125,000 dilution of SYBR® Green I (Molecular Probes Cat. No. S7563) 20 nM fluorescein calibration dye (BioRad) and 0.5 units of Platinum Taq Polymerase (Invitrogen). A Corbett RotorGene 3000 was set to run at 95 C for 2 minutes then 5 cycles of 95 C 15 seconds-65 C 3 minutes, and then 45 cycles of 95 C 5 seconds-65 C 30 seconds.

The mismatch primer MycRM1 allows detection of hypomethylated myc DNA in K562 DNA compared to the fully-methylated DNA of CpGenome. It also allows the detection of the reduced methylation at the HpaII site in the colorectal cancer tumour sample 35/03 as compared to its matched normal sample 34/03. (See FIG. 5B).

EXAMPLE 4

Insertion Template Oligonucleotide

This example shows that selection can be achieved without using a terminal 3' mismatch in the primer, but rather an insertion placed several nucleotides from the 3' end. Such 'insertion template oligonucleotides may be particularly suited to cases in which the targeted restriction site is present in a repetitive sequence that might vary in sequence at the point of extension.

In cases where a repeat sequence class has great sequence heterogeneity, a mismatch primer designed to a consensus sequence may actually completely match a significant number of mutant sequences. This would cause selective enrichment of the mutants and reduce the selective power of ES-PCR. For such cases a modification of the method was developed that involved designing primers that have short insertions or deletions compared to the repeat class consensus sequence. It was reasoned that very few or no mutant sequences would have the same length deletion or insertion with the same sequence and at the same position. Although some of the 3' bases match the target (6 in the case shown) the deletion (or insertion in the case shown here) will prevent proper positioning of the 3' end, thus delaying extension.

In this example, two HpaII sites within the 5' (promoter) region of LINE retrotransposable element is targeted. Selection for sequences that have been cut at both HpaII sites is achieved by using two insertion template oligonucleotides/primers as shown in FIG. 6A.

5 ng of DNA treated with DraI (recognition site TTTAAA, not methylation sensitive) and HpaII (CCGG, methylation-sensitive) was tested. PCRs were carried out in 25 microlitres of 20 mM Tris-HCl (pH 8.4), 50 mM KCl, 2.7 mM MgCl$_2$, 400 mM Betaine, 0.2 mM dCTP, 0.2 mM dGTP, 0.2 mM dATP, 0.4 mM dUTP, 10 nM MLHJ65 selective primer, 200 nM insertion primers, 50 nM HEX-labelled LPAHex probe, 1/125,000 dilution of SYBR® Green I (Molecular Probes Cat. No. S7563) 20 nM fluorosein calibration dye (BioRad), and 0.5 units of Platinum Taq Polymerase (Invitrogen). A Corbett RotorGene 3000 was set to run at 95 C for 2 minutes then 5 cycles of (95 C 15 seconds, 60 C 20 seconds, 65 C 3 minutes), and then 50 cycles of (95 C 15 seconds, 65 C 30 seconds).

As seen in FIG. 6B amplification from substantially hypomethylated K562 DNA was seen approximately 14 cycles ahead of amplification from fully methylated DNA.

EXAMPLE 5

3' Blocked Template Oligonucleotide

Figure 7B:
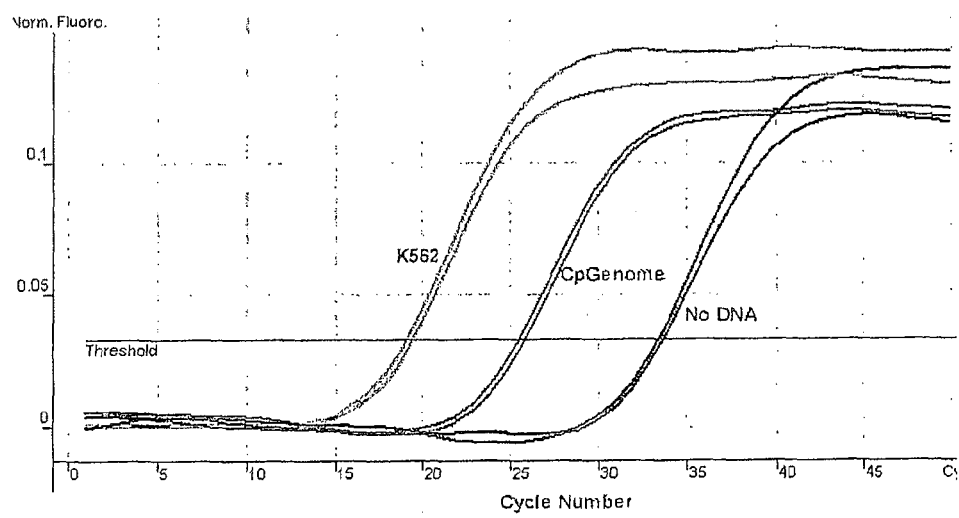
FIG. 7B: Amplification curves and Table showing Ct values for amplification from substantially hypomethylated K562 DNA or from methylated CpGenome DNA.

The first BstUI site in the consensus sequence of Alu elements was targeted using the template oligonucleotide and primers shown in FIG. 7A. The template oligonucleotide BAFMLJ15 is unable to be extended due to being blocked with a phosphate group at its 3' end. The part of the oligonucleotide that is boxed has the same sequence as the JOE-LUX 'third' oligonucleotide and allows the eventual incorporation of JOELUX into the PCR product. JOELUX carries a JOE fluorescent moiety attached near the 3' end whose fluorescence increases when present in double stranded DNA.

PCRs were carried out in 25 microlitres of 20 mM Tris-HCl (pH 8.4), 50 mM KCl, 2.7 mM $MgCl_2$, 0.2 mM dCTP, 0.2 mM dGTP, 0.2 mM dATP, 0.4 mM dUTP, 40 nM AluRev21, 10 nM BAFMLJ15, 60 nM JOELUX primer, 1/125,000 dilution of SYBR® Green I (Molecular Probes Cat. No. S7563) 20 nM fluorosein calibration dye (BioRad) 1 unit of BstUI (New England Biolabs) and 1 unit of Platinum Taq Polymerase (Invitrogen). A Corbett RotorGene 3000 was set to run at 37 C for 5 minutes, 95 C for 2 minutes then 5 cycles of 95 C 1 minute-60 C 40 seconds, and then 45 cycles of 95 C 15 seconds-68 C 20 seconds.

Using the single phosphate-blocked template primer amplification from substantially hypomethylated K562 DNA is delayed by over six PCR cycles relative to amplification from the methylated CpGenome DNA.

EXAMPLE 6

Use of ES-PCR in Selection of Methylated DNA

Figure 8B:
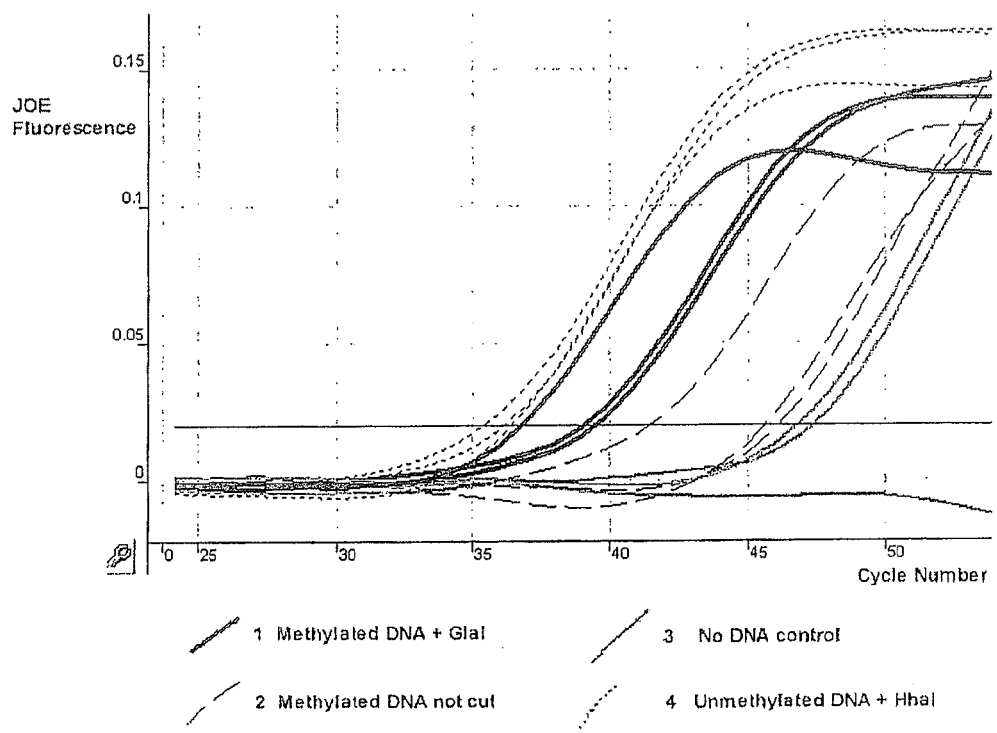
FIG. 8B: Amplification curves and Table showing Ct values for amplification of methylated CpGenome DNA or unmethylated DNA.

The region targeted is a GlaI site within the CpG island (chr3:37009233-37010360 in hg17 freeze) of the hMLH1 gene (FIG. 8A). According to a publication of the company Sibenzyme GlaI cuts the sequence GCGC only when the internal C is methylated. Full activity of GlaI is only seen when all four C's of its recognition site are methylated. Thus GlaI only exhibits full activity on fully methylated DNA at the site CGCGCG. This site is found at position chr3:37,009,348-37,009,353within the CpG island of the hMLH1 gene.

Fully methylated DNA 'CpGenome' was obtained from Chemicon. This DNA had been enzymatically methylated at all CpG sites and was treated with GlaI. As a control, unmethylated DNA was isolated from blood and treated with the restriction enzyme HhaI. This enzyme recognizes the same site but only cuts when the site is unmethylated. (Note that there are two HhaI sites next to one another at this location.) The template oligonucleotide used to select for cut ends was MLHJ65. This oligonucleotide has a 5' extension that allows incorporation of a JOE-labelled LUX primer, JOELUX. It also has 3 mismatches at its 3' end, two of which are converted to abasic sites when digested by uracil DNA glycosylase. An unmodified primer MLHRev3 served as reverse primer (see FIG. 8A).

1 ug of fully methylated DNA (from Chemicon) was treated with 16 units of GlaI for 2 hours at 37 C in 50 uL of 1×SEBuffer Y (33 mM Tris-acetate, 66 mM potassium acetate, 10 mM magnesium acetate, 1 mM dithiothreitol pH 7.9@25° C.)+100 ug/ml Bovine Serum Albumin. 20 units of a second restriction enzyme, DraI was also included in the reaction. This enzyme recognizes the sequence TTTAAA and thus cuts DNA regardless of methylation status. After heat inactivation (70 C for 15 minutes) 140 uL TEX (10 mM Tris HCl, 0.1 mM EDTA, 0.01% Triton X-100) and 10 uL of 50 mM EDTA was added, giving 5 ng/uL concentration of DNA. The uncut control was treated in the same way, except that 50% glycerol was added in place of the restriction enzyme. Blood DNA cut by HhaI was prepared in the same way, except that New England Biolabs Buffer 3 (50 mM Tris-HCl, 10 mM $MgCl_2$, 100 mM NaCl, 1 mM DTT (pH 7.9 at 25° C.) and 20 units of HhaI was used.

5 ng of cut or uncut DNA was tested. PCRs were carried out in 25 microlitres of 20 mM Tris-HCl (pH 8.4), 50 mM KCl, 4 mM $MgCl_2$, 800 mM Betaine, 0.2 mM dNTPs, 10 nM MLHJ65 selective primer, 200 nM MLHRev3 reverse primer, 40 nM JOELUX fluorescent LUX primer, SYBR® Green I (Molecular Probes Cat. No. S7563) 20 nM fluorescein calibration dye (BioRad), 0.02 units of Uracil DNA Glycosylase (New England Biolabs) and 0.5 units of Platinum Taq Polymerase (Invitrogen). A Corbett RotorGene 3000 was set to run at 95 C for 90 seconds then 5 cycles of (95 C 30 seconds, 60 C 10 seconds, 72 C 30 seconds), and then 55 cycles of (95 C 1 second-60 C 10 seconds, 72 C 30 seconds). Tests were done in triplicate.

Methylated DNA that had been cut with GlaI amplified an average of 6 cycles ahead of uncut methylated DNA. The control unmethylated DNA cut with HhaI amplified an average of 8.4 cycles ahead of uncut DNA. The data show that in both cases where the DNA was cut to produce specific ends amplification was significantly favoured compared with uncut DNA. The earlier amplification of the HhaI-cut DNA may relate to the different cutting efficiencies of the HhaI and GlaI enzymes.

EXAMPLE 7

Detection of a Point Mutation in the BRAF Gene

Mutation in the BRAF gene is common in colorectal cancer and nearly always involves V00E mutation caused by a T to A transversion (Chan et al. 2003). ES-PCR was used in a two step procedure to differentiate mutant and normal sequences in DNA from blood and the colorectal cancer cell line WiDr respectively. In the first PCR round a primer BRFMX containing two mismatches (FIG. 9A(i); mismatches underlined) 5' CCTCACAGTAAAAATAGGT-GATTTTGGTCTAGCTCTAG 3' (SEQ ID NO:7) was used to introduce a XbaI restriction site that depended on the presence of the A base at the mutation site (FIG. 9A(ii); mutation site underlined).

Primer BRFMX was used in PCR with a reverse primer BRFR1, to amplify the target region. The sequence of the resultant amplified DNA is shown, with the XbaI site underlined in FIG. 9A(iii).

In the second round, The ES-PCR primer BRFU was used in combination with an outer overlapping JOELUX primer and a reverse primer BRFR2 (FIG. 9B). The copied top strand is not shown in FIG. 9B because XbaI gives a 4 base overhang which when copied will give multiple mismatches with the selective oligonucleotide BRFU and thus should not be involved in the reaction. The bottom strand is written 3' to 5' for BRAF-A after cutting with XbaI and denaturation. Extension of the BRFU foligo is inhibited by the 3 terminal base mismatches (underlined); no Uracil DNA Glycosylase was used in this experiment so extension of BRFU is only prevented by the 3 terminal mismatches (FIG. 9B).

2 uL of a 1/100 dilution of each of the first round products was digested with 5 units of XbaI is in NEB2 buffer plus BSA for two hours at 37° C. 1 uL of each of the digested products was used in the ESPCR. PCRs were carried out in 25 microlitres of 20 mM Tris-HCl (pH 8.4), 50 mM KCl, 4 mM $MgCl_2$, 0.2 mM dNTPs, 10 nM BRFU selective oligonucleotide, 100 nM BRFR2 reverse primer, 40 nM JOELUX fluorescent LUX primer, SYBR® Green I (Molecular Probes Cat. No. S7563) 20 nM fluorescein calibration dye (BioRad) and 0.5 units of Platinum Taq Polymerase (Invitrogen). A Corbett RotorGene 3000 was set to run at 95° C. for 90 seconds then 5 cycles of (95° C. 30 seconds, 50° C. 40 seconds, 65° C. 10 seconds), and then 40 cycles of (95° C. 5 seconds, 65° C. 15 seconds). Tests were done in duplicate.

Figure 9C:
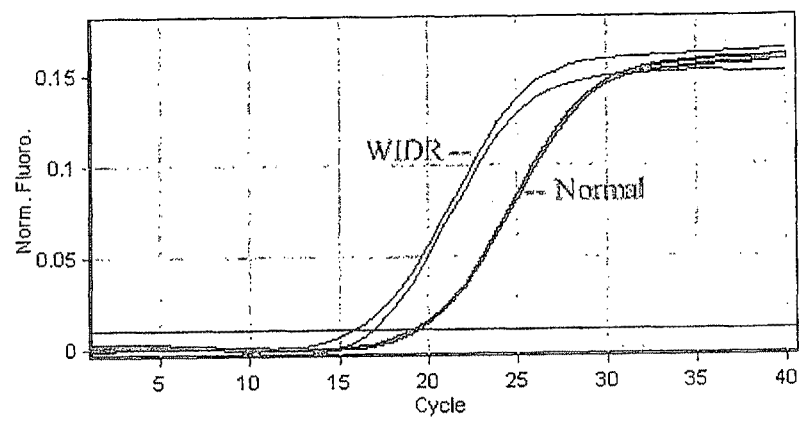
FIG. 9C: Amplification curves showing selective amplification of the mutated BRAF gene in the colorectal cancer cell line WiDr.

Amplification, measured by JOE fluorescence is shown in FIG. 9C. The earlier amplification seen in the case of the sample derived from WiDr shows that ES-PCR can be used to detect a mutation.

EXAMPLE 8

Use of Restriction Enzymes that Cleave Outside their Recognition Sequence in the Generation of Nucleic Acid Molecules that Differ in Sequence Adjacent their 3' Terminus A number of restriction enzymes (Type IIs, Type III and Type IV) cleave DNA outside their recognition sites at defined distances, herein referred to as "flanking cutters". The 3' termini generated by flanking cutters therefore differ between sites and depend on the sequence flanking the enzyme recognition site. At a given cleavage site, such an enzyme will also produce different ends if there has been an insertion or deletion of bases between the recognition site and the cleavage site. The different sequences produced adjacent to the cleavage site provide a basis for selective amplification of deletion or insertion forms using ES-PCR or other selective amplification approaches. Previously, methods for the detection of a deletion or insertion have relied on changes in DNA fragment length following restriction enzyme digestion. The approach presently described utilises the difference in nucleic acid sequence of restriction enzyme fragments, resulting from the presence of a deletion or an insertion between a restriction enzyme's recognition sequence and its cleavage site causing a shift in the cleavage site for restriction enzymes that cleave at a defined distance from their recognition sequence.

8.1 Determination of a Deletion or Insertion in a Short Homopolymer Run.
 8.1.1. A deletion or insertion in a short homopolymer run of As adjacent to a Bbr7I restriction site (GAAGAC (7/11) (FIG. 10A(i)) is detected using either ES-PCR (FIG. 10A(iv)) (see Section 8.1.1.1 below) or by using a specific primer following extension of the 3' terminus using terminal transferase (FIGS. 10A(ii) and 10A(iii)). The primer shown in FIG. 10A(iii) matches the product of the shorter original DNA molecule and will prime effectively, while it forms a 3 base mismatch with the product of the longer molecule and will not prime. The product of the shorter molecule can be then amplified using a suitable reverse primer from within the sequence.
 8.1.1.1 Amplification by ES-PCR. The cleaved lower strand from the short molecule ('short sequence', FIG. 10A(i)) will prime effectively on a template oligonucleotide having complementary nucleic acid sequence in its 3' region and an amine blocked 3' end. The newly incorporated terminal sequence resulting from 3' extension of the targeted molecule can be used in combination with an internal second oligonucleotide for amplification during ES-PCR. In contrast the cleaved end from the long molecule ('long sequence', FIG. 10A(i)) has a 3 base mismatch, and will therefore not prime on the template oligonucleotide and so be refractory to amplification.

8.2. A second example is shown in FIG. 10B. Most enzymes with cutting sites outside their recognition sequence cleave to give staggered ends which can act as substrates for linker ligation and subsequent PCR. In the present example an MmeI site (TCCGAC (20/18)) is adjacent to a short mononucleotide run (FIG. 10B(i)). The cut site is 20 bases from the recognition site on the top strand and 18 on the bottom strand. Variants of the sequence with 10 or 9 Ts are shown. The ends generated when cut with MmeI are shown in FIG. 10B(ii). To selectively amplify the "nine" molecule a linker with a CA 3' extension as shown can be ligated, as shown in FIG. 10B(iii). This molecule could be detected by PCR, wherein the forward primer would have the sequence as shown in FIG. 10B (iii) in combination with a reverse primer from within the region to be amplified. The alternate "ten" molecule gives a mismatching end that will ligate poorly and its amplification will be further compromised by mismatching with the primer.

8.2.1 Amplification by ES-PCR. Alternatively, the 3' termini generated can be discriminated using ES-PCR with the template oligonucleotide shown in FIG. 10C. The "nine" molecule perfectly matches the 3' region of the template oligonucleotide and will therefore prime on it, while the "ten" molecule produces a mismatch at its 3' terminus, thereby preventing 3' extension complementary to the 5' tail of the template oligonucleotide, and thereby failing to be amplified in the reaction.

In many instances an endogenous site will not be suitably located for a restriction enzyme that cuts outside its recognition sequence. In such cases it is possible to introduce an appropriate site either using a primer to introduce mutations to produce a site flanking the region of interest and to analyse the resulting PCR product as a two step procedure. Alternatively, if there is another closely located restriction site, a new site can be introduced by cutting with the first enzyme and ligating an adaptor containing the desired enzyme site. In the example of FIG. 10B the sequence shown is derived from a site within the TGFRB2 gene, where a single base deletion in the sequence of a stretch of ten As is common in colorectal cancer. The MmeI site is notionally introduced by cutting at a flanking EcoRII site and ligating an adaptor containing the MmeI site.

Microsatellite sequences provide an example of clinical relevance where it is desired to detect instability of short simple repeats, normally by detecting the presence of shorter, deleted forms (Example 8.3.)

The presence of an insertion can also be detected as shown in Example 8.4

8.3: Detection of Deletion in Microsatellite NR22.

The microsatellite NR-22 was described by Suraweera et al (2002). An MboII restriction site is located next to the mononucleotide repeat of the microsatellite (FIG. 11A(i)). MboII cuts at a distance from its recognition site, GAAGA, 8 nucleotides from the end of its recognition sequence on the top strand and 7 nucleotides away on the bottom strand. The sequence adjacent to the resulting new end will depend upon the length of the mononucleotide repeat. In FIGS. 11A(ii) and 11A(iii) only the bottom strand is shown for simplicity. In practice, the upper strand is also taken into account because during the PCR it is copied, giving a new, extendable 3' end. Examples are shown for the length of 22 (normal) 20, 18 and 16 base pairs. (Cloning and sequencing of this region from the colorectal cancer cell line HCT116 gave lengths of 16 by and 18 by for the NR-22 mononucleotide repeat.).

Two templating oligonucleotides are shown in FIGS. 11A (ii) and 11A(iii), respectively, aligned with the MboII cut DNA (bottom strand) derived from mononucleotide repeats of different length from 16 to 22 bases. Extension of the template oligonucleotides on genomic DNA is prevented or reduced by the presence of mismatches at the 3' end, as well as abasic sites after cleavage by Uracil DNA Glycosylase of the U-containing oligonucleotides. FIG. 11A(ii) shows the control template oligonucleotide 04FNR22-0. Products of cutting repeats of different length are all able to prime on F1NR22-0 and the extended product will subsequently be amplified by the LUX primer, FAMLUX1. Amplification from the shorter repeats may be less efficient due to the shorter length of the hybridizing region. The second template oligonucleotide J5NR22-4 is designed to selectively allow amplification only from shorter repeat sequences. The underlined bases at the 3' end of the MboII-cut DNA from repeats of 20 or 22 bases form mismatches with the template oligonucleotide and will prevent their extension. In contrast, the ends derived from shorter repeats of 16 or 18 bases will prime efficiently leading to subsequent amplification by the JOE-LUX5 primer and detection by JOE fluorescence.

In summary, the normal length of the NR-22 microsatellite is expected to only give FAM fluorescence in the PCR whereas deletions of NR-22 such as 4 bp or 6 pb will give both FAM and JOE fluorescence.

PCRs were carried out in 25 microlitres of 20 mM Tris-HCl (pH 8.4), 50 mM KCl, 4 mM MgCl2, 0.2 mM dNTPs, 2 nM F1NR22-0, 10 nM J5NR22-4, 80 nM NR22R1, 80 nM JOE-LUX5 fluorescent LUX primer, 20 nM FAMLUX1 fluorescent LUX primer, 0.04 units of Uracil DNA Glycosylase (New England Biolabs), 0.5 units MboII restriction endonuclease (New England Biolabs), 0.5 units of Platinum Taq Polymerase (Invitrogen). A Corbett RotorGene 3000 was set to run at 37 C for 5 minutes, 95 C for 90 seconds, then 5 cycles of (95 C 10 seconds, 60 C 40 seconds, 70 C 10 seconds), and then 60 cycles of (95 C 5 seconds, 70 C 15 seconds). JOE and FAM fluorescence was monitored. Tests were done in duplicate. 5 nanograms of DNA isolated from either the cell line HCT116 or from blood of a normal subject were added to the reactions.

As seen in FIG. 11B, in the case of FAM fluorescence (FIG. 11B(i)), the blood DNA is amplified ahead of the DNA from HCT116 cells that carry deletions within the NR-22 microsatellite. Also, FAM fluorescence in the case of the blood DNA is higher at the end of the reaction. This suggests that this assay could be developed into an end point assay, one that does not require access to a real time PCR machine. In the case of HCT116, both FAM and JOE reactions will occur because the deletions in this cell line will allow copying of both of the template oligonucleotides in the reaction. However the template oligonucleotide that is specific for the deletion-carrying DNA is used at a higher concentration so biasing toward the JOE reaction. Because the reverse primer NR22R1 is used at only 80 nM it is expected that the two reactions will compete with one another, explaining the difference in ultimate FAM signal between the two input DNAs. In the case of the JOE signal (FIG. 11B(ii)), only the deleted DNA from HCT116 gives MboII-cut strands able to prime on the J5NR22-4 template oligonucleotide carrying the tail that allows JOELUX5 incorporation.

8.4: Detection of Insertions.

Figure 12A:
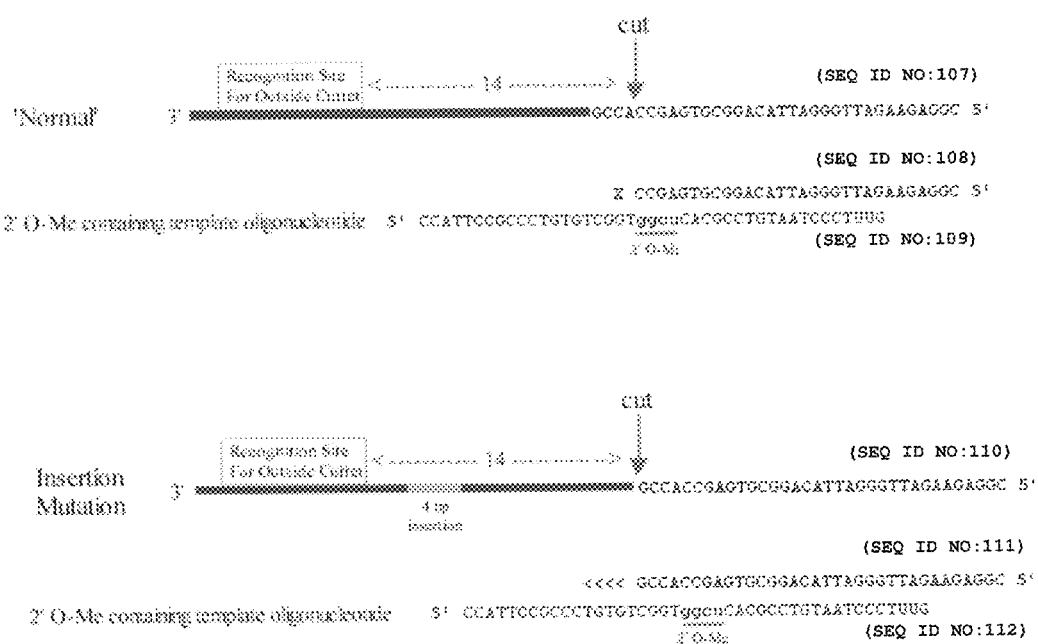
FIG. 12A: Scheme showing digestion with a restriction enzyme having a cleavage site at a defined distance outside of its recognition sequence, and a shift in the cleavage site due to a 4 bp insertion between the recognition sequence and the cleavage site. 3' extension of digested DNA will only occur if an insertion exists between the recognition sequence and the cleavage site due to the presence of 2' O-methyl nucleotides (underlined) in the template oligonucleotide that block 3' extension of the digested DNA when the 2' O-methyl nucleotides hybridise at the 3' terminus of digested DNA. In the case of DNA having an insertion, the site of cleavage is shifted such that the 2' O-methyl nucleotides of the template oligonucleotide no longer hybridise at the 3' terminus.

In FIG. 12A, only the bottom strand of a DNA fragment is shown for simplicity (although it should be remembered that restriction enzymes in general cut double stranded DNA). The location of a restriction enzyme recognition site (not to scale) is shown. An example of a restriction enzyme that cuts outside of its recognition site is AcuI, which cuts at a distance of 14 from the end of its recognition site when considering the 'bottom' strand.

A template oligonucleotide is designed such that when after hybridization to the cut end, extension on the template oligonucleotide is reduced or blocked by the presence of one or more 2' O-Methyl nucleotides. Other means to block extension are well known to those skilled in the art, such as use of abasic sites in the template oligonucleotide or the use of mismatches (as described herein). Extension is prevented in this case because the 3' end of the cut DNA hybridized not to a DNA nucleotide but to a 2' O-Methyl nucleotide.

An example of an insertion mutation is shown in the bottom part of FIG. 12A. Insertion of 4 base pairs between the recognition site for an outside cutter such as AcuI and its cut site will shift the cut position 4 base pairs to the left. When the resulting cut DNA hybridizes to the 2' O-Methyl-containing template oligonucleotide the resulting complex has a stretch of 4 DNA-DNA matched nucleotides thus allowing extension of the cut 3' end.

Data to show the efficacy of this approach were obtained by employing synthetic oligonucleotides that mimic the different cut bottom strands that would be generated from cutting either 'normal' DNA or DNA containing either a 1 bp or 4 bp insertion (FIG. 12B).

The PCR is eventually driven by the two outside primers, JOELUX and CommR5. JOELUX is a LUX primer labelled with JOE. It matches 15 nucleotides of the template oligonucleotide and is thus incorporated after the template oligonucleotide is copied. CommR5 has 11 nucleotides in common with the test oligonucleotides and can become incorporated after JOELUX copies a test oligonucleotide.

PCRs were carried out in 25 microlitres of 20 mM Tris-HCl (pH 8.4), 50 mM KCl, 4 mM MgCl$_2$, 0.2 mM dNTPs, 10nM template oligonucleotide, 40 nM JOELUX fluorescent LUX primer, 200 nM CommR5, $10^8$ test oligonucleotide, 0.04 units of Uracil DNA Glycosylase (New England Biolabs) 0.5 units of Platinum Taq Polymerase (Invitrogen). A Corbett RotorGene 3000 was set to run at 37° C. for 5 minutes, 95° C. for 90 seconds, then 5 cycles of (95° C. 30 seconds, 55° C. 40 seconds, 65° C. 15 seconds), and then 55 cycles of (95° C. 5 seconds, 65° C. 15 seconds). JOE fluorescence was detected. Tests were done in triplicate. The 5 minute incubation at 37° C. was to allow time for digestion with Uracil DNA Glycosylase.

It can be seen in FIG. 12C that amplification of $10^8$ test oligonucleotide (continuous lines) that corresponds to the bottom strand of 'Normal' DNA after cutting with the outside cutter is only evident after cycle 30. Test oligonucleotides corresponding to insertions of 1 base pair (dotted lines) or 4 base pairs (dashed lines) are amplified about 10 cycles earlier, showing that this experimental setup could be used to selectively amplify DNA from insertion mutants.

EXAMPLE 9

Template Oligonucleotide Designs

A model system was used to assess modifications of template oligonucleotide for usefulness in the methods of the invention. Two test DNAs were prepared and used as targets. The target DNA named 'Cut' corresponds to the bottom strand of an Alu element that has been cut by the restriction enzyme BstUI. Successful cutting of Alu elements at the BstUI site only occurs if this site is unmethylated. In this experiment no restriction enzymes are used because target oligonucleotide 'mimics' are employed. The second target DNA is called 'Uncut' and is a mimic of a fragment cut or broken at a position different from where BstUI cuts, having an extension of 5 Ts. Both target oligonucleotides are shown in the 3' to 5' orientation in FIG. 13A. AluRev is the reverse primer. It fully matches its target sequence and is also shown in the 3' to 5' orientation.

AluPhB and a series of related oligonucleotides were used as templating oligonucleotides (FIG. 13A). These are shown in the 5' to 3' orientation. Extension of AluPhB is prevented by the presence of a phosphate at the 3' end instead of the normal OH group. AluPhB has a 5' tail (underlined, FIG. 13A) that once copied by extension of a target sequence adjacent a 3' terminus, allows incorporation of the JOE-labelled outer primer called JOELUX. PCR amplification was monitored by JOE fluorescence as the primer becomes incorporated in the PCR product.

PCRs were carried out in 25 microlitres of 20 mM Tris-HCl (pH 8.4), 50 mM KCl, 4 mM MgCl2, 0.2 mM dNTPs, 10 nM template oligonucleotide (AluPhB or other), 40 nM AluRev, 40 nM JOELUX fluorescent LUX primer, 0.04 units of Uracil DNA Glycosylase (New England Biolabs) 0.5 units of Platinum Taq Polymerase (Invitrogen). A Corbett RotorGene 3000 was set to run at 37° C. for 5 minutes, 95° C. for 2 minutes, then 5 cycles of (95° C. 10 seconds, 60° C. 40 seconds, 70° C. 5 seconds), and then 40 cycles of (95° C. 1 second, 65° C. 15 seconds). JOE fluorescence was detected. Tests were done in duplicate. The 5 minute incubation at 37° C. was only included so that cycling conditions were identical to other experiments in which restriction enzyme digestion prior to PCR was required. This made comparison of results from the different experiments more straightforward. The Uracil DNA Glycosylase (UDG) was added to the reaction to digest the template oligonucleotide that contains U nucleotides. To each reaction either $10^7$ Cut or $10^{10}$ Uncut target DNA were added.

The reference template oligonucleotide AluPhB has a 23 base hybridising region with the "cut" target sequence and is blocked for extension by a phosphate at its 3' end. FIG. 13C(i) shows amplification from $10^7$ "cut" molecules and 1000 fold higher amount of the "uncut" molecule. If there were no selectivity we would expect about a delay of about 10 cycles in amplification from the "cut" molecules. Amplification at an equivalent cycle number is indicative of about 1000 fold selectivity. The degree of selectivity may be limited either by extension of the template oligonucleotide (eg if the 3' phosphate is removed or if the template oligonucleotide is nicked) or by mispriming of the "uncut" molecules on the template oligonucleotide, in this case by mispriming on AluPhB. Alternative template oligonucleotides have been developed that show improved selectivity because of certain incorporated features.

The series of alternate template oligonucleotides differ in the 3' modifications designed to prevent extension of the template oligonucleotide. The modifications shown include incorporating a C7 amine or a C3 spacer or a 3 base terminal mismatch (AluUUG, where the two Us will form abasic sites after UDG treatment) and/or internal modifications that provide a block to extension if there is aberrant priming from upstream of the proper priming site. These include 2' O-Methyl modified bases in AluMeAm and AluMeMult (bold lower case), inclusion of an abasic site (X in AluAbSp) or of uracil bases that can be converted to abasic sites by treatment with UDG (FIG. 13B).

Incorporation of extension blocking modifications in the template oligonucleotide substantially inhibited amplification from the "uncut" molecules, leading 1000 fold or greater selectivity. Comparison of AluMeAm and AluMeMult shows a selectivity with a greater number of modified bases, though their presence is probably also reducing the efficiency of correct priming.

The sequence of AluHL is such that its 5' and 3' ends can form a hairpin structure (with the 3' end having multiple mismatches with the target "cut' molecule that will prevent it priming. The hairpin structure possibly prevents both mispriming by the template oligonucleotide and mispriming on the template oligonucleotide by the "uncut" nucleic acid molecule.

These experiments show that template oligonucleotides can be prevented from extension in different ways, and modifications that reduce or prevent copying of the hybridizing portion of the templating oligonucleotides can increase the specificity of the ES-PCR.

References

Chan, T. L.; Zhao, W.; Leung, S. Y., and Yuen, S. T. BRAF and KRAS mutations in colorectal hyperplastic polyps and serrated adenomas. Cancer Res. 2003 Aug. 15; 63(16) 4878-81

Elnifro E M, Ashshi A M, Cooper R J, Klapper P E. Multiplex PCR: optimization and application in diagnostic virology. Clin Microbiol Rev. 2000 October; 13(4):559-70.

Mueller P R and B Wold. In vivo footprinting of a muscle specific enhancer by ligation mediated PCR. Science. 1989 Nov. 10; 246(4931):780-6. Erratum in: Science 1990 May 18; 248(4957):802.

Pfeifer G P, Steigerwald S D, Mueller P R, Wold B, Riggs A D. Genomic sequencing and methylation analysis by ligation mediated PCR. Science. 1989 Nov. 10; 246(4931): 810-3.

Schumacher A, Kapranov P, Kaminsky Z, Flanagan J, Assadzadeh A, Yau P, Virtanen C, Winegarden N, Cheng J, Gingeras T, Petronis A. Microarray-based DNA methylation profiling: technology and applications. Nucleic Acids Res. 2006 Jan. 20; 34(2):528-42.

Sharrard R M, Royds J A, Rogers S, Shorthouse A J. Patterns of methylation of the c-myc gene in human colorectal cancer progression. Br. J. Cancer 1992 65:667-672

Steigerwald S D, Pfeifer G P, Riggs A D. Ligation-mediated PCR improves the sensitivity of methylation analysis by restriction enzymes and detection of specific DNA strand breaks. Nucleic Acids Res. 1990 Mar. 25; 18(6):1435-9.

Suraweera, N., Duval, A., Reperant, M., Vaury, C., Furlan, D., Leroy, K., Seruca, R., Iacopetta, B. and Hamelin, R. Evaluation of Tumor Microsatellite Istability Using Five Quasimonomorphic Mononucleotide Repeats and Pentaplex PCR, Gastroenterology 2002 123(6):1804-1811

Wittwer C T, Herrmann M G, Gundry C N, Elenitoba-Johnson K S. Real-time multiplex PCR assays. Methods. 2001 December; 25(4):430-42.

The claims defining the invention are as follows:

1. A method for selective amplification from a sample of a nucleic acid molecule having a target sequence adjacent a 3' terminus, in the presence of molecules comprising the target sequence not adjacent a 3' terminus but embedded within the molecule, the method comprising (i) contacting the sample with a template oligonucleotide having
(a) a 3' region substantially complementary to the target sequence adjacent the 3' terminus of a nucleic acid molecule;
(b) a 5' tail comprising a nucleic acid sequence such that a free 5' tail is formed when the template oligonucleotide anneals to the target sequence located adjacent a 3' terminus or embedded within a nucleic acid molecule, the 5' tail providing a template for extension of the 3' terminus of the target sequence incorporating sequence complementary to the 5' tail of the template oligonucleotide resulting in the addition of sequence complementary to the 5' tail to the target sequence; and (c) a modification in the 3' region that delays 3' extension of said template oligonucleotide;

(ii) contacting the sample with a second oligonucleotide for priming in a reverse direction to the template oligonucleotide, and optionally a third oligonucleotide sharing nucleotide sequence with the 5' tail of the template oligonucleotide;

(iii) carrying out amplification of the sample wherein (a) annealing of the template oligonucleotide to target sequence adjacent a 3' terminus is stabilised over annealing of said oligonucleotide to target sequence not adjacent to a 3' terminus by copying of the 5' tail of the template oligonucleotide by extension from the 3' terminus of the target sequence in the presence of delayed 3' extension of said oligonucleotide; and (b) wherein consequent stabilised annealing of the template oligonucleotide to target sequence adjacent to a 3' terminus enhances efficiency of 3' extension of the template oligonucleotide compared to extension of the template oligonucleotide annealed to target sequence not adjacent a 3' terminus, and (c) wherein amplification occurs using the template oligonucleotide and/or the third oligonucleotide in combination with the second oligonucleotide, resulting in selective amplification of target sequence adjacent a 3' terminus in the presence of nucleic acid molecules comprising target sequence embedded within the molecule.

2. A method for selective amplification from a sample, of a nucleic acid molecule having a target sequence adjacent a 3' terminus the result of cleavage of the molecule, in the presence of uncleaved molecules comprising the target sequence embedded within the molecule, the method comprising:

(i) contacting the sample with a template oligonucleotide having (a) a 3' region substantially complementary to the target sequence adjacent the 3' terminus of a nucleic acid molecule; and (b) a 5' tail of comprising a nucleic acid sequence such that a free 5' tail is formed when the template oligonucleotide anneals to cleaved or uncleaved nucleic acid molecules, the 5' tail providing a template for extension of the 3' terminus of the target sequence incorporating sequence complementary to the 5' tail of the template oligonucleotide resulting in the addition of sequence complementary to the 5' tail to the target sequence; and (c) a modification in the 3' region that delays 3' extension of the template oligonucleotide;

(ii) contacting the sample with a second oligonucleotide for priming in a reverse direction to the template oligonucleotide, and optionally a third oligonucleotide sharing nucleotide sequence with the 5' tail of the template oligonucleotide;

(iii) carrying out amplification of the sample wherein (a) annealing of the template oligonucleotide to target sequence adjacent a 3' terminus the result of cleavage of a nucleic acid molecule, is stabilised over annealing of said oligonucleotide to target sequence not adjacent a 3' terminus in an uncleaved nucleic acid molecule by copying of the 5' tail of the template oligonucleotide by extension from the 3' terminus of the target sequence in the presence of delayed 3' extension of said oligonucleotide; and (b) wherein consequent stabilised annealing of the template oligonucleotide to the cleaved nucleic acid molecule enhances efficiency of 3' extension of the template oligonucleotide compared to extension of said oligonucleotide annealed to an uncleaved nucleic acid molecule, and (c) wherein amplification occurs using the template oligonucleotide and/or the third oligonucleotide in combination with the second oligonucleotide, resulting in selective amplification of target sequence adjacent to a 3' terminus over target sequence embedded within a nucleic acid molecule, resulting in selective amplification of cleaved nucleic acid molecules over uncleaved nucleic acid molecules.

3. A method for selective amplification from a sample of a nucleic acid molecule having a target sequence adjacent a 3' terminus, in the presence of a mixed population of molecules having differing 3' termini, the method comprising (i) contacting the sample with a template oligonucleotide having (a) a 3' region substantially complementary to the target sequence adjacent the 3' terminus; and (b) a 5' tail comprising a nucleic acid sequence such that a free 5' tail is formed when the template oligonucleotide anneals to the target sequence adjacent a 3' terminus, the 5' tail providing a template for extension of the 3' terminus of the target sequence incorporating sequence complementary to the 5' tail of the template oligonucleotide resulting in the addition of sequence complementary to the 5' tail to the target sequence; and (c) a modification in the 3' region that delays 3' extension of said oligonucleotide;

(ii) contacting the sample with a second oligonucleotide for priming in a reverse direction to the template oligonucleotide, and optionally a third oligonucleotide sharing nucleotide sequence with the 5' tail of the template oligonucleotide;

(iii) carrying out amplification of the sample wherein (a) specific annealing of the template oligonucleotide to target sequence adjacent a 3' terminus is stabilised over annealing of template oligonucleotide to non-complementary sequence adjacent a 3' terminus, by copying of the 5' tail of the template oligonucleotide by extension from the 3' terminus of the target sequence in the presence of delayed 3' extension of the template oligonucleotide; and (b) wherein consequent stabilised annealing of the template oligonucleotide to the target sequence adjacent a 3' terminus enhances efficiency of 3' extension of the template oligonucleotide compared to extension of said oligonucleotide annealed to non-complementary sequence adjacent a 3' terminus, and (c) wherein amplification occurs using the template oligonucleotide and/or the third oligonucleotide in combination with the second oligonucleotide, resulting in selective amplification of target sequence adjacent a 3' terminus in the presence of a mixed population of 3' termini.

4. The method according to any one of claims 1-3, wherein a modification in the 3' region of the template oligonucleotide that delays 3' extension of the oligonucleotide is selected from the group consisting of
   (i) the incorporation of a 3' terminal nucleotide mismatch,
   (ii) the incorporation of one or more nucleotide mismatches in the 3' region of the template oligonucleotide close to the 3' terminus,
   (iii) the incorporation of a deletion in the 3' region of the template oligonucleotide close to the 3' terminus,
   (iv) the incorporation of an insertion in the 3' region of the template oligonucleotide close to the 3' terminus, and
   (v) any combination of modifications (i)-(iv).

5. The method according to claim 4, wherein the modification in the 3' region of the template oligonucleotide is the incorporation of a 3' terminal nucleotide mismatch.

6. The method according to claim 4, wherein the modification in the 3' region of the template oligonucleotide is the incorporation of an insertion in the 3' region of the template oligonucleotide close to the 3' terminus.

7. A method for selective amplification from a sample of a nucleic acid molecule having a target sequence adjacent a 3' terminus in the presence of molecules comprising the target sequence not adjacent a 3' terminus but embedded within the molecule, the method comprising
   (i) contacting the sample with a template oligonucleotide having
      (a) a 3' region substantially complementary to the target sequence adjacent the 3' terminus a nucleic acid molecule ; and
      (b) a 5' tail comprising a nucleic acid sequence such that a free 5' tail is formed when the template oligonucleotide anneals to target sequence located adjacent a 3' terminus or embedded within a nucleic acid molecule, the 5' tail providing a template for extension of the 3' terminus of the target sequence incorporating sequence complementary to the 5' tail of the template oligonucleotide resulting in the addition of sequence complementary to the 5' tail to the target sequence; and
      (c) a modification in the 3' region that blocks 3' extension of said template oligonucleotide, or, a modification in the hybridizing region of the template oligonucleotide that permits 3' extension but hinders or blocks copying in the 3' region of said oligonucleotide;
   (ii) contacting the sample with a second oligonucleotide for priming in a reverse direction to the template oligonucleotide;
   (iii) contacting the DNA sample with a third oligonucleotide sharing nucleotide sequence with the 5' tail of the template oligonucleotide and from which 3' extension proceeds unhindered;
   (iv) carrying out amplification of the sample wherein
      (a) annealing of the template oligonucleotide to nucleic acid molecules in the sample is followed by copying of the 5' tail of the template oligonucleotide when the template oligonucleotide anneals to target sequence adjacent a 3' terminus but not when the template oligonucleotide anneals to target sequence embedded within a nucleic acid molecule, in the presence of blocked 3' extension of the template oligonucleotide, or, in the presence of unhindered 3' extension of a template oligonucleotide from which subsequent copying is hindered or blocked; and
      (b) wherein amplification proceeds with the second and third oligonucleotides, selectively amplifying target sequence located adjacent a 3' terminus by virtue of the copied 5' tail, amplification of target sequence embedded within a nucleic acid molecule not proceeding due to the absence of copying of the 5' tail and either blocked 3' extension of the template oligonucleotide, or blocked copying of the template oligonucleotide.

8. A method for selective amplification from a sample, of a nucleic acid molecule having a target sequence adjacent a 3' terminus the result of cleavage of the molecule, in the presence of uncleaved nucleic acid molecules comprising the target sequence embedded within the molecule, the method comprising:
   (i) contacting the DNA sample with a template oligonucleotide having
      (a) a 3' region substantially complementary to the target sequence adjacent the 3' terminus of a nucleic acid molecule; and
      (b) a 5' tail comprising a nucleic acid sequence such that a free 5' tail is formed when the template oligonucleotide anneals to cleaved or uncleaved nucleic acid molecules, the 5' tail providing a template for extension of the 3' terminus of the target sequence incorporating sequence complementary to the 5' tail of the template oligonucleotide resulting in the addition of sequence complementary to the 5' tail to the target sequence; and
      (c) a 3' modification that blocks 3' extension of said template oligonucleotide; or, a modification in the hybridizing region of the template oligonucleotide that permits 3' extension but hinders or blocks copying in the 3' region of said oligonucleotide;
   (ii) contacting the sample with a second oligonucleotide for priming in a reverse direction to the template oligonucleotide;
   (iii) contacting the sample with a third oligonucleotide sharing nucleotide sequence with the 5' tail of the template oligonucleotide and from which 3' extension proceeds unhindered;
   (iv) carrying out amplification of the sample in which
      (a) annealing of the template oligonucleotide to target sequence adjacent a 3' terminus the result of cleavage of a nucleic acid molecule is followed by copying of the 5' tail of the template oligonucleotide but not when the template oligonucleotide anneals to target sequence embedded within an uncleaved nucleic acid molecule, in the presence of blocked 3' extension of said oligonucleotide, or, in the presence of unhindered 3' extension of a template oligonucleotide from which subsequent copying is hindered or blocked; and
      (b) wherein amplification proceeds with the second and third oligonucleotides, selectively amplifying target sequence adjacent a 3' terminus by virtue of the copied 5' tail sequence, amplification of target sequence embedded within an uncleaved molecule not proceeding due to the absence of copying of the 5' tail and either blocked 3' extension of the template oligonucleotide, or blocked copying of the template oligonucleotide, resulting in selective amplification of cleaved nucleic acid molecules over uncleaved nucleic acid molecules.

9. A method for selective amplification from a sample of a nucleic acid molecule having a target sequence adjacent a 3' terminus, in the presence of a mixed population of 3' termini, the method comprising (i) contacting the sample with a template oligonucleotide having
  (a) a 3' region substantially complementary to the target sequence adjacent the 3' terminus; and
  (b) a 5' tail comprising a nucleic acid sequence such that a free 5' tail is formed when the template oligonucleotide anneals to the target sequence adjacent a 3' terminus, the 5' tail providing a template for extension of the 3' terminus of the target sequence incorporating sequence complementary to the 5' tail of the template oligonucleotide resulting in the addition of sequence complementary to the 5' tail to the target sequence; and
  (c) a modification in the 3' region that blocks 3' extension of the template oligonucleotide, or, a modification in the hybridizing region of the template oligonucleotide that permits 3' extension but hinders or blocks copying in the 3' region of said oligonucleotide;
(ii) contacting the sample with a second oligonucleotide for priming in a reverse direction to the template oligonucleotide;
(iii) contacting the DNA sample with a third oligonucleotide sharing nucleotide sequence with the 5' tail of the template oligonucleotide and from which 3' extension proceeds unhindered;
(iv) carrying out amplification of the sample wherein
  (a) specific annealing of the template oligonucleotide to target sequence is followed by copying of the 5' tail of the template oligonucleotide when the template oligonucleotide anneals to target sequence adjacent a 3' terminus but not when the template oligonucleotide anneals to non-complementary sequence adjacent a 3' terminus, in the presence of blocked 3' extension of the template oligonucleotide, or, in the presence of unhindered 3' extension of a template oligonucleotide from which subsequent copying is hindered or blocked; and
  (b) wherein amplification proceeds with the second and third oligonucleotides selectively amplifying target sequence located adjacent a 3' terminus by virtue of the copied 5' tail sequence, amplification of non-complementary sequence adjacent a 3' terminus not proceeding due to the absence of copying of the 5' tail and either blocked 3' extension of the template oligonucleotide, or blocked copying of the template oligonucleotide, resulting in selective amplification of target sequence adjacent a 3' terminus in the presence of a mixed population of 3' termini.

10. The method according to any one of claims 7-9, wherein the modification in the 3' region of the template oligonucleotide that blocks 3' extension of the template oligonucleotide is selected from the group consisting of
  (i) the incorporation of one or more non-extendible moieties or nucleotide analogues at its 3' terminus,
  (ii) the incorporation of a combination of a 3' terminal non-extendible moieties or nucleotide analogue and one or more nucleotide mismatches in the 3' region of the template oligonucleotide close to its 3' terminus,
  (iii) the incorporation of one or more abasic sites in the 3' region of the template oligonucleotide close to its 3' terminus, and
  (iv) the incorporation of a combination of one or more abasic sites and one or more nucleotide mismatches in the 3' region of the template oligonucleotide close to its 3' terminus.

11. The method according to claim 10, wherein the one or more non-extendible moieties or nucleotide analogues are selected from the group consisting of
  (i) a 2', 3' dideoxynucleotide,
  (ii) a 3' C3, C18 or other length spacer,
  (iii) a 3' phosphorylated nucleotide,
  (iv) a peptide nucleic acid base,
  (v) an amine linker,
  (vi) one or more uracils treated with Uracil_DNA glycosylase,
  (vii) RNA,
  (viii) one or more 2' O-Methyl RNA residues, and
  (ix) any combination of (i)-(viii).

12. The method according to claim 11, wherein the non-extendible base is an amine linker.

13. The method according to claim 11, wherein the non-extendible base is a C3 spacer.

14. The method according to claim 11, wherein the non-extendible base is one or more uracils treated with Uracil_DNA glycosylase.

15. The method according to claim 11, wherein the non-extendible base is one or more 2' O-Methyl RNA residues.

16. The method according to claim 10, wherein the non-extendible base is one or more abasic sites in the 3' region of the template oligonucleotide close to the 3' terminus.

17. The method according to any one of claims 7-9, wherein a modification in the 3' region that that permits 3' extension but hinders or blocks copying in the 3' region of said oligonucleotide is selected from the group consisting of
  (i) the insertion within the 3' region of the template oligonucleotide of one or more base analogues,
  (ii) the insertion of one or more RNA nucleotides,
  (iii) the insertion of one or more abasic sites, and
  (iv) any combination of (i)-(iii).

18. The method according to claim 17, wherein the modification is the insertion of one or more base analogues.

19. The method according to claim 17, wherein the modification is the insertion of one or more abasic sites.

20. The method according to claim 9, wherein the 3' termini of the nucleic acid molecules in the sample including the 3' terminus of the targeted nucleic acid molecule, are a result of digestion of the sample with a flanking cutter restriction endonuclease.

21. The method according to claim 20, wherein the modification in the 3' region that blocks 3' extension of said template oligonucleotide is the incorporation of one or more base analogues, one or more abasic sites or any combination of these at its 3' terminus.

22. The method according to claim 20 or 21, wherein the template oligonucleotide further incorporates a modification in the 3' region that blocks 3' extension of the target sequence.

23. The method according to claim 22, wherein the modification is the incorporation in the 3' region of the template oligonucleotide of one or more base analogues.

24. The method according to claim 23, wherein the template oligonucleotide incorporates a 3' terminal nucleotide mismatch, one or more abasic sites and the incorporation of one or more base analogues.

25. The method according to any one of claims 1-3 and 7-9, wherein the second oligonucleotide is a further template oligonucleotide.

26. The method according to any one of claims 1-3 and 7-9, wherein the nucleic acid molecules comprise DNA.

27. The method according to claim 2 or claim 8, wherein cleavage of the nucleic acid molecule is the result of cleavage by a sequence-specific restriction endonuclease.

28. The method according to claim 27, wherein the restriction endonuclease is a sequence-specific methylation sensitive restriction endonuclease.

29. The method according to claim 28, wherein the methylation sensitive restriction endonuclease is inhibited by DNA methylation.

30. The method according to claim 29, wherein the methylation sensitive restriction endonuclease is selected from the group consisting of HpaII, HhaI, BstuI, NotI, SmaI and SacII.

31. The method according to claim 28, wherein the methylation sensitive restriction endonuclease cleaves methylated DNA.

32. The method according to claim 31, wherein the methylation sensitive restriction endonuclease is selected from the group consisting of GlaI and BisI.

33. The method according to claim 27, wherein the restriction endonuclease is chosen to distinguish between the presence or absence of a restriction site in the nucleic acid molecules in the sample.

34. A method for detecting the presence or absence of a deletion or insertion in a nucleic acid molecule in a sample wherein the deletion or insertion occurs between a restriction enzyme recognition site and its cleavage site located outside the recognition site at a defined distance, the method comprising
   (i) digesting the sample with the restriction enzyme having a cleavage site outside its recognition site at a defined distance, and
   (ii) determining the nucleotide sequence adjacent a 3' terminus generated by cleavage wherein the nucleotide sequence adjacent the 3' terminus will depend on the presence or absence of a deletion or insertion, and wherein a shift in the cleavage site either in the 3' or 5' direction will occur in the presence of a deletion or insertion, respectively.

35. The method according to claim 34, wherein step (ii) is achieved by a method according to claim 3 or claim 9.

* * * * *

UNITED STATES PATENT AND TRADEMARK OFFICE
CERTIFICATE OF CORRECTION

PATENT NO.        : 8,501,403 B2                    Page 1 of 1
APPLICATION NO.   : 12/294891
DATED             : August 6, 2013
INVENTOR(S)       : Molloy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1226 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 133

<210> SEQ ID NO 1
<211> LENGTH: 74
<212> TYPE: DNA
<213> ORGANISM: Homo sapiens

<400> SEQUENCE: 1
gcgtggctgt ctccactgag tcccgggcac gggtcaggct aaccgcggga ggaatttaat    60
ctagagttta actt    74

<210> SEQ ID NO 2
<211> LENGTH: 30
<212> TYPE: DNA
<213> ORGANISM: artificial
<220> FEATURE:
<223> OTHER INFORMATION: forward primer

<400> SEQUENCE: 2
cactcccact cgggaggaat ttaatctagc    30

<210> SEQ ID NO 3
<211> LENGTH: 18
<212> TYPE: DNA
<213> ORGANISM: artificial
<220> FEATURE:
<223> OTHER INFORMATION: reverse primer

<400> SEQUENCE: 3
acccgtgccc gggactca    18

<210> SEQ ID NO 4
<211> LENGTH: 20
<212> TYPE: DNA
<213> ORGANISM: artificial
<220> FEATURE:
<223> OTHER INFORMATION: 21qTRHEX 5' HEX

<400> SEQUENCE: 4
ccgtgcccgg gactcagtgg    20

<210> SEQ ID NO 5
<211> LENGTH: 24
<212> TYPE: DNA
<213> ORGANISM: artificial
<220> FEATURE:
<223> OTHER INFORMATION: 21qTRM13 5'

<400> SEQUENCE: 5
ccctcacact cggttagcct gact    24

<210> SEQ ID NO 6
<211> LENGTH: 71
<212> TYPE: DNA
<213> ORGANISM: Homo sapiens

<400> SEQUENCE: 6
gagcgccaga ggaggaacga gctaaaacgg agctttttg ccctgcgtga ccagatcccg    60
gagttggaaa a    71

<210> SEQ ID NO 7
<211> LENGTH: 38
<212> TYPE: DNA
<213> ORGANISM: artificial
<220> FEATURE:
<223> OTHER INFORMATION: BRFMX

<400> SEQUENCE: 7
cctcacagta aaaataggtg attttggtct agctctag    38

```
<210> SEQ ID NO 8
<211> LENGTH: 6
<212> TYPE: DNA
<213> ORGANISM: artificial
<220> FEATURE:
<223> OTHER INFORMATION: Bbr71

<400> SEQUENCE: 8 gaagac                                                                     6

<210> SEQ ID NO 9
<211> LENGTH: 6
<212> TYPE: DNA
<213> ORGANISM: artificial
<220> FEATURE:
<223> OTHER INFORMATION: MmeI

<400> SEQUENCE: 9 tccgac                                                                     6

<210> SEQ ID NO 10
<211> LENGTH: 5
<212> TYPE: DNA
<213> ORGANISM: artificial
<220> FEATURE:
<223> OTHER INFORMATION: Mbo1

<400> SEQUENCE: 10 gaaga                                                                      5

<210> SEQ ID NO 11
<211> LENGTH: 18
<212> TYPE: DNA
<213> ORGANISM: artificial
<220> FEATURE:
<223> OTHER INFORMATION: primer

<400> SEQUENCE: 11
acccgtgccc gggactca                                                       18

<210> SEQ ID NO 12
<211> LENGTH: 74
<212> TYPE: DNA
<213> ORGANISM: artificial
<220> FEATURE:
<223> OTHER INFORMATION: 21qTRC

<400> SEQUENCE: 12
cgggaggaat ttaatctaga gtctaacttg cgtggctgtc cccactgagt cccgggcacg         60
ggtcaggcta accg                                                           74

<210> SEQ ID NO 13
<211> LENGTH: 74
<212> TYPE: DNA
<213> ORGANISM: artificial
<220> FEATURE:
<223> OTHER INFORMATION: 21qTFMLHC/T

<400> SEQUENCE: 13
gccctcctta aattagatct cagattgaac gcaccgacag gggtgactca gggcccgtgc         60
ccagtccgat tggc                                                           74

<210> SEQ ID NO 14
<211> LENGTH: 30
<212> TYPE: DNA
<213> ORGANISM: artificial
```

<220> FEATURE:
<223> OTHER INFORMATION: primer

<400> SEQUENCE: 14
cactcccact cgggaggaat ttaatctagc                                          30

<210> SEQ ID NO 15
<211> LENGTH: 84
<212> TYPE: DNA
<213> ORGANISM: artificial
<220> FEATURE:
<223> OTHER INFORMATION: 21qTFMLHC/T

<400> SEQUENCE: 15
aggctaaccg cgggaggaat ttaatctaga gtctaacttg cgtggctgtc cccactgagt        60
cccgggcacg ggtcaggcta accg                                               84

<210> SEQ ID NO 16
<211> LENGTH: 84
<212> TYPE: DNA
<213> ORGANISM: artificial
<220> FEATURE:
<223> OTHER INFORMATION: 21qTRC

<400> SEQUENCE: 16
tccgattggc gccctcctta aattagatct cagattgaac gcaccgacag gggtgactca        60
gggcccgtgc ccagtccgat tggc                                               84

<210> SEQ ID NO 17
<211> LENGTH: 30
<212> TYPE: DNA
<213> ORGANISM: artificial
<220> FEATURE:
<223> OTHER INFORMATION: primer

<400> SEQUENCE: 17
cactcccact cgggaggaat ttaatctagc                                          30

<210> SEQ ID NO 18
<211> LENGTH: 30
<212> TYPE: DNA
<213> ORGANISM: artificial
<220> FEATURE:
<223> OTHER INFORMATION: 21qTFMLHC/T

<400> SEQUENCE: 18
cactcccact cgggaggaat ttaatctagc                                          30

<210> SEQ ID NO 19
<211> LENGTH: 74
<212> TYPE: DNA
<213> ORGANISM: artificial
<220> FEATURE:
<223> OTHER INFORMATION: 21qTRM13

<400> SEQUENCE: 19
cgggaggaat ttaatctaga gtctaacttg cgtggctgtc cccactgagt cccgggcacg        60
ggtcaggcta accg                                                          74

<210> SEQ ID NO 20
<211> LENGTH: 24
<212> TYPE: DNA
<213> ORGANISM: artificial
<220> FEATURE:
<223> OTHER INFORMATION: primer

```
<400> SEQUENCE: 20
ccctcacact cggttagcct gact                                              24

<210> SEQ ID NO 21
<211> LENGTH: 71
<212> TYPE: DNA
<213> ORGANISM: artificial
<220> FEATURE:
<223> OTHER INFORMATION: Myc Uncut 5'

<400> SEQUENCE: 21
gagcgccaga ggaggaacga gctaaaacgg agcttttttg ccctgcgtga ccagatcccg       60
gagttggaaa a                                                           71

<210> SEQ ID NO 22
<211> LENGTH: 22
<212> TYPE: DNA
<213> ORGANISM: artificial
<220> FEATURE:
<223> OTHER INFORMATION: primer

<400> SEQUENCE: 22
cgccagagga ggaacgagct aa                                                22

<210> SEQ ID NO 23
<211> LENGTH: 58
<212> TYPE: DNA
<213> ORGANISM: artificial
<220> FEATURE:
<223> OTHER INFORMATION: Myc HpaII cut

<400> SEQUENCE: 23
gagcgccaga ggaggaacga gctaaaacgg agcttttttg ccctgcgtga ccagatcc         58

<210> SEQ ID NO 24
<211> LENGTH: 25
<212> TYPE: DNA
<213> ORGANISM: artificial
<220> FEATURE:
<223> OTHER INFORMATION: primer

<400> SEQUENCE: 24
cctcgtccct ggatctggtc acgcc                                             25

<210> SEQ ID NO 25
<211> LENGTH: 18
<212> TYPE: DNA
<213> ORGANISM: artificial
<220> FEATURE:
<223> OTHER INFORMATION: Line uncut 5'-3'
<220> FEATURE:
<221> NAME/KEY: misc_feature
<222> LOCATION: (1)..(4)
<223> OTHER INFORMATION: n is a, c, g, or t

<400> SEQUENCE: 25
nnnnccggtc tacagctc                                                     18

<210> SEQ ID NO 26
<211> LENGTH: 40
<212> TYPE: DNA
<213> ORGANISM: artificial
<220> FEATURE:
<223> OTHER INFORMATION: Line uncut 5'-3'
```

```
<400> SEQUENCE: 26
ccagcgtgag cgacgcagaa gacgggtgat ttctgcattt                              40

<210> SEQ ID NO 27
<211> LENGTH: 20
<212> TYPE: DNA
<213> ORGANISM: artificial
<220> FEATURE:
<223> OTHER INFORMATION: Line uncut 5'-3'
<220> FEATURE:
<221> NAME/KEY: misc_feature
<222> LOCATION: (17)..(20)
<223> OTHER INFORMATION: n is a, c, g, or t

<400> SEQUENCE: 27
ccatctgagg taccggnnnn                                                    20

<210> SEQ ID NO 28
<211> LENGTH: 18
<212> TYPE: DNA
<213> ORGANISM: artificial
<220> FEATURE:
<223> OTHER INFORMATION: Line uncut 3'-5'
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (15)..(18)
<223> OTHER INFORMATION: n is a, c, g, or t

<400> SEQUENCE: 28
gagctgtaga ccggnnnn                                                      18

<210> SEQ ID NO 29
<211> LENGTH: 40
<212> TYPE: DNA
<213> ORGANISM: artificial
<220> FEATURE:
<223> OTHER INFORMATION: Line uncut 3'-5'

<400> SEQUENCE: 29
aaatgcagaa atcacccgtc ttctgcgtcg ctcacgctgg                              40

<210> SEQ ID NO 30
<211> LENGTH: 20
<212> TYPE: DNA
<213> ORGANISM: artificial
<220> FEATURE:
<223> OTHER INFORMATION: Line uncut 3'-5'
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t

<400> SEQUENCE: 30
nnnnccggta cctcagatgg                                                    20

<210> SEQ ID NO 31
<211> LENGTH: 13
<212> TYPE: DNA
<213> ORGANISM: artificial
<220> FEATURE:
<223> OTHER INFORMATION: Line HpaII cut 5'-3'
```

<400> SEQUENCE: 31
cggtctacag ctc                                                          13

<210> SEQ ID NO 32
<211> LENGTH: 40
<212> TYPE: DNA
<213> ORGANISM: artificial
<220> FEATURE:
<223> OTHER INFORMATION: Line HpaII cut 5'-3'

<400> SEQUENCE: 32
ccagcgtgag cgacgcagaa gacgggtgat ttctgcattt                             40

<210> SEQ ID NO 33
<211> LENGTH: 15
<212> TYPE: DNA
<213> ORGANISM: artificial
<220> FEATURE:
<223> OTHER INFORMATION: Line HpaII cut 5'-3'

<400> SEQUENCE: 33
ccatctgagg taccg                                                        15

<210> SEQ ID NO 34
<211> LENGTH: 13
<212> TYPE: DNA
<213> ORGANISM: artificial
<220> FEATURE:
<223> OTHER INFORMATION: Line HpaII cut 3'-5'

<400> SEQUENCE: 34
gagctgtaga ccg                                                          13

<210> SEQ ID NO 35
<211> LENGTH: 40
<212> TYPE: DNA
<213> ORGANISM: artificial
<220> FEATURE:
<223> OTHER INFORMATION: Line HpaII cut 3'-5'

<400> SEQUENCE: 35
aaatgcagaa atcaccctgtc ttctgcgtcg ctcacgctgg                            40

<210> SEQ ID NO 36
<211> LENGTH: 16
<212> TYPE: DNA
<213> ORGANISM: artificial
<220> FEATURE:
<223> OTHER INFORMATION: Line HpaII cut 3'-5'

<400> SEQUENCE: 36
cggtacctca mgatgg                                                       16

<210> SEQ ID NO 37
<211> LENGTH: 25
<212> TYPE: DNA
<213> ORGANISM: artificial
<220> FEATURE:
<223> OTHER INFORMATION: LPA Hex Probe

<400> SEQUENCE: 37
gtctttagtg ggcagaagac gcagc                                             25

```
<210> SEQ ID NO 38
<211> LENGTH: 32
<212> TYPE: DNA
<213> ORGANISM: artificial
<220> FEATURE:
<223> OTHER INFORMATION: LIFES36

<400> SEQUENCE: 38
cacgcagggt cggtctacag ctcgtgccag cg                          32

<210> SEQ ID NO 39
<211> LENGTH: 34
<212> TYPE: DNA
<213> ORGANISM: artificial
<220> FEATURE:
<223> OTHER INFORMATION: LIRE13

<400> SEQUENCE: 39
cctgcagcct cggtacctca gatgggtcaa atgc                        34

<210> SEQ ID NO 40
<211> LENGTH: 27
<212> TYPE: DNA
<213> ORGANISM: artificial
<220> FEATURE:
<223> OTHER INFORMATION: JOELUX

<400> SEQUENCE: 40
cacaggttct caccattccg ccctgtg                                27

<210> SEQ ID NO 41
<211> LENGTH: 31
<212> TYPE: DNA
<213> ORGANISM: artificial
<220> FEATURE:
<223> OTHER INFORMATION: BAFMLJ15

<400> SEQUENCE: 41
ccattccgcc ctgtgtcggt ggctcacgcc t                           31

<210> SEQ ID NO 42
<211> LENGTH: 46
<212> TYPE: DNA
<213> ORGANISM: artificial
<220> FEATURE:
<223> OTHER INFORMATION: BstUI-cut 5'-3'

<400> SEQUENCE: 42
cggtggctca cgcctgtaat cccagcactt tgggaggccg aggcgg           46

<210> SEQ ID NO 43
<211> LENGTH: 46
<212> TYPE: DNA
<213> ORGANISM: artificial
<220> FEATURE:
<223> OTHER INFORMATION: BstU1-cut 3'-5'

<400> SEQUENCE: 43
gccaccgagt gcggacatta gggtcgtgaa accctccggc tccgcc           46

<210> SEQ ID NO 44
<211> LENGTH: 21
<212> TYPE: DNA
<213> ORGANISM: artificial
<220> FEATURE:
<223> OTHER INFORMATION: AluRev21
```

-continued

```
<400> SEQUENCE: 44
gcctcggcct cccaaagtgc t                                            21

<210> SEQ ID NO 45
<211> LENGTH: 38
<212> TYPE: DNA
<213> ORGANISM: artificial
<220> FEATURE:
<223> OTHER INFORMATION: BRFMX5'-3'

<400> SEQUENCE: 45
cctcacagta aaataggtg attttggtct agctctag                           38

<210> SEQ ID NO 46
<211> LENGTH: 63
<212> TYPE: DNA
<213> ORGANISM: artificial
<220> FEATURE:
<223> OTHER INFORMATION: BRFMX5'-3'

<400> SEQUENCE: 46
cctcacagta aaataggtg attttggtct agctacagtg aaatctcgat ggagtgggtc   60
cca                                                                63

<210> SEQ ID NO 47
<211> LENGTH: 26
<212> TYPE: DNA
<213> ORGANISM: artificial
<220> FEATURE:
<223> OTHER INFORMATION: BRFR1 5'-3'

<400> SEQUENCE: 47
aatggatcca gacaactgtt caaact                                       26

<210> SEQ ID NO 48
<211> LENGTH: 63
<212> TYPE: DNA
<213> ORGANISM: artificial
<220> FEATURE:
<223> OTHER INFORMATION: BRAF-T(WT)

<400> SEQUENCE: 48
cctcacagta aaataggtg attttggtct agctctagtg aaatctcgat ggagtgggtc   60
cca                                                                63

<210> SEQ ID NO 49
<211> LENGTH: 63
<212> TYPE: DNA
<213> ORGANISM: artificial
<220> FEATURE:
<223> OTHER INFORMATION: BRAF-A (Mutant)

<400> SEQUENCE: 49
cctcacagta aaataggtg attttggtct agctctagag aaatctcgat ggagtgggtc   60
cca                                                                63

<210> SEQ ID NO 50
<211> LENGTH: 20
<212> TYPE: DNA
<213> ORGANISM: artificial
<220> FEATURE:
<223> OTHER INFORMATION: BRF2
```

```
<400> SEQUENCE: 50
gttcaaactg atgggaccca                                              20

<210> SEQ ID NO 51
<211> LENGTH: 36
<212> TYPE: DNA
<213> ORGANISM: artificial
<220> FEATURE:
<223> OTHER INFORMATION: BRAE-A

<400> SEQUENCE: 51
gttcaaactg atgggaccca ctccatcgag atttct                            36

<210> SEQ ID NO 52
<211> LENGTH: 28
<212> TYPE: DNA
<213> ORGANISM: artificial
<220> FEATURE:
<223> OTHER INFORMATION: BRFU 5'

<400> SEQUENCE: 52
ccgccctgtg cagaaatctc gatgguug                                     28

<210> SEQ ID NO 53
<211> LENGTH: 27
<212> TYPE: DNA
<213> ORGANISM: artificial
<220> FEATURE:
<223> OTHER INFORMATION: JOELUX 5'

<400> SEQUENCE: 53
cacaggttct caccattccg ccctgtg                                      27

<210> SEQ ID NO 54
<211> LENGTH: 13
<212> TYPE: DNA
<213> ORGANISM: artificial
<220> FEATURE:
<223> OTHER INFORMATION: Enzyme cleavage short 3'

<400> SEQUENCE: 54
gaagacactt ttt                                                     13

<210> SEQ ID NO 55
<211> LENGTH: 17
<212> TYPE: DNA
<213> ORGANISM: artificial
<220> FEATURE:
<223> OTHER INFORMATION: Enzyme cleavage short 3'

<400> SEQUENCE: 55
tttttttcag ccttctg                                                 17

<210> SEQ ID NO 56
<211> LENGTH: 17
<212> TYPE: DNA
<213> ORGANISM: artificial
<220> FEATURE:
<223> OTHER INFORMATION: Enzyme cleavage short 3'

<400> SEQUENCE: 56
aaaaaaaaag tgtcttc                                                 17
```

```
<210> SEQ ID NO 57
<211> LENGTH: 13
<212> TYPE: DNA
<213> ORGANISM: artificial
<220> FEATURE:
<223> OTHER INFORMATION: Enzyme cleaveage short 3'

<400> SEQUENCE: 57
ctgaaggctg aaa                                                        13

<210> SEQ ID NO 58
<211> LENGTH: 13
<212> TYPE: DNA
<213> ORGANISM: artificial
<220> FEATURE:
<223> OTHER INFORMATION: Enzyme cleavage long 3'

<400> SEQUENCE: 58
gaagacactt ttt                                                        13

<210> SEQ ID NO 59
<211> LENGTH: 20
<212> TYPE: DNA
<213> ORGANISM: artificial
<220> FEATURE:
<223> OTHER INFORMATION: Enzyme cleavage long 3'

<400> SEQUENCE: 59
tttttttttt cagccttctg                                                 20

<210> SEQ ID NO 60
<211> LENGTH: 17
<212> TYPE: DNA
<213> ORGANISM: artificial
<220> FEATURE:
<223> OTHER INFORMATION: Enzyme cleavage long 3'

<400> SEQUENCE: 60
aaaaaaaaag tgtcttc                                                    17

<210> SEQ ID NO 61
<211> LENGTH: 16
<212> TYPE: DNA
<213> ORGANISM: artificial
<220> FEATURE:
<223> OTHER INFORMATION: Enzyme cleavage long 3'

<400> SEQUENCE: 61
ctgaaggctg aaaaaa                                                     16

<210> SEQ ID NO 62
<211> LENGTH: 23
<212> TYPE: DNA
<213> ORGANISM: artificial
<220> FEATURE:
<223> OTHER INFORMATION: Terminal transferase short 3'

<400> SEQUENCE: 62
ctgaaggctg aaattttttt ttt                                             23

<210> SEQ ID NO 63
<211> LENGTH: 26
<212> TYPE: DNA
<213> ORGANISM: artificial
<220> FEATURE:
<223> OTHER INFORMATION: Terminal transferase long 3'
```

-continued

```
<400> SEQUENCE: 63
ctgaaggctg aaaaaatttt tttttt                                            26

<210> SEQ ID NO 64
<211> LENGTH: 23
<212> TYPE: DNA
<213> ORGANISM: artificial
<220> FEATURE:
<223> OTHER INFORMATION: Selective priming short 3'

<400> SEQUENCE: 64
ctgaaggctg aaatttttt ttt                                                23

<210> SEQ ID NO 65
<211> LENGTH: 16
<212> TYPE: DNA
<213> ORGANISM: artificial
<220> FEATURE:
<223> OTHER INFORMATION: Selective priming short 5'

<400> SEQUENCE: 65
aaaaaaaaaa tttcag                                                       16

<210> SEQ ID NO 66
<211> LENGTH: 26
<212> TYPE: DNA
<213> ORGANISM: artificial
<220> FEATURE:
<223> OTHER INFORMATION: Selective priming lont 3'

<400> SEQUENCE: 66
ctgaaggctg aaaaaatttt tttttt                                            26

<210> SEQ ID NO 67
<211> LENGTH: 16
<212> TYPE: DNA
<213> ORGANISM: artificial
<220> FEATURE:
<223> OTHER INFORMATION: Selective priming long 5'

<400> SEQUENCE: 67
aaaaaaaaaa tttcag                                                       16

<210> SEQ ID NO 68
<211> LENGTH: 13
<212> TYPE: DNA
<213> ORGANISM: artificial
<220> FEATURE:
<223> OTHER INFORMATION: ES-PCR short 3'-5'

<400> SEQUENCE: 68
ctgaaggctg aaa                                                          13

<210> SEQ ID NO 69
<211> LENGTH: 33
<212> TYPE: DNA
<213> ORGANISM: artificial
<220> FEATURE:
<223> OTHER INFORMATION: ES-PCR template oligo 5'-3'

<400> SEQUENCE: 69
accattccgc cctgtgcgga tttcagcctt cag                                    33
```

-continued

<210> SEQ ID NO 70
<211> LENGTH: 16
<212> TYPE: DNA
<213> ORGANISM: artificial
<220> FEATURE:
<223> OTHER INFORMATION: ES-PCR long 3'-5'

<400> SEQUENCE: 70
ctgaaggctg aaaaaa                                                  16

<210> SEQ ID NO 71
<211> LENGTH: 58
<212> TYPE: DNA
<213> ORGANISM: artificial
<220> FEATURE:
<223> OTHER INFORMATION: Ten Ts

<400> SEQUENCE: 71
ccgcgttatc cgaccaggct ttttttttc cttcataatg cactttggag aagcagca     58

<210> SEQ ID NO 72
<211> LENGTH: 58
<212> TYPE: DNA
<213> ORGANISM: artificial
<220> FEATURE:
<223> OTHER INFORMATION: Ten Ts

<400> SEQUENCE: 72
ggcgcaatag gctggtccga aaaaaaaaag gaagtattac gtgaaacctc ttcgtcgt    58

<210> SEQ ID NO 73
<211> LENGTH: 57
<212> TYPE: DNA
<213> ORGANISM: artificial
<220> FEATURE:
<223> OTHER INFORMATION: Nine Ts

<400> SEQUENCE: 73
ccgcgttatc cgaccaggct tttttttcc ttcataatgc actttggaga agcagca      57

<210> SEQ ID NO 74
<211> LENGTH: 57
<212> TYPE: DNA
<213> ORGANISM: artificial
<220> FEATURE:
<223> OTHER INFORMATION: Nine Ts

<400> SEQUENCE: 74
ggcgcaatag gctggtccga aaaaaaaagg aagtattacg tgaaacctct tcgtcgt     57

<210> SEQ ID NO 75
<211> LENGTH: 24
<212> TYPE: DNA
<213> ORGANISM: artificial
<220> FEATURE:
<223> OTHER INFORMATION: MmI ten 5'

<400> SEQUENCE: 75
ataatgcact ttggagaagc agca                                         24

<210> SEQ ID NO 76
<211> LENGTH: 26
<212> TYPE: DNA
<213> ORGANISM: artificial
<220> FEATURE:
<223> OTHER INFORMATION: MmeI Ten 3'

```
<400> SEQUENCE: 76
tgctgcttct ccaaagtgca ttatga                                           26

<210> SEQ ID NO 77
<211> LENGTH: 23
<212> TYPE: DNA
<213> ORGANISM: artificial
<220> FEATURE:
<223> OTHER INFORMATION: MmeI Nine 5'

<400> SEQUENCE: 77
taatgcactt tggagaagca gca                                              23

<210> SEQ ID NO 78
<211> LENGTH: 25
<212> TYPE: DNA
<213> ORGANISM: artificial
<220> FEATURE:
<223> OTHER INFORMATION: MmeI Nine 3'

<400> SEQUENCE: 78
tgctgcttct ccaaagtgca ttatg                                            25

<210> SEQ ID NO 79
<211> LENGTH: 16
<212> TYPE: DNA
<213> ORGANISM: artificial
<220> FEATURE:
<223> OTHER INFORMATION: linker

<400> SEQUENCE: 79
caccgaccgt cgagca                                                      16

<210> SEQ ID NO 80
<211> LENGTH: 23
<212> TYPE: DNA
<213> ORGANISM: artificial
<220> FEATURE:
<223> OTHER INFORMATION: linker

<400> SEQUENCE: 80
taatgcactt tggagaagca gca                                              23

<210> SEQ ID NO 81
<211> LENGTH: 14
<212> TYPE: DNA
<213> ORGANISM: artificial
<220> FEATURE:
<223> OTHER INFORMATION: linker

<400> SEQUENCE: 81
ctcgacggtc ggtg                                                        14

<210> SEQ ID NO 82
<211> LENGTH: 25
<212> TYPE: DNA
<213> ORGANISM: artificial
<220> FEATURE:
<223> OTHER INFORMATION: linker

<400> SEQUENCE: 82
tgctgcttct ccaaagtgca ttatg                                            25
```

-continued

<210> SEQ ID NO 83
<211> LENGTH: 22
<212> TYPE: DNA
<213> ORGANISM: artificial
<220> FEATURE:
<223> OTHER INFORMATION: Forward primer

<400> SEQUENCE: 83
caccgaccgt cgagtcataa tg                                         22

<210> SEQ ID NO 84
<211> LENGTH: 26
<212> TYPE: DNA
<213> ORGANISM: artificial
<220> FEATURE:
<223> OTHER INFORMATION: NH2 3'

<400> SEQUENCE: 84
tgctgcttct ccaaagtgca ttatga                                     26

<210> SEQ ID NO 85
<211> LENGTH: 35
<212> TYPE: DNA
<213> ORGANISM: artificial
<220> FEATURE:
<223> OTHER INFORMATION: NH2 5'

<400> SEQUENCE: 85
accattccgc cctgtgcgga acataatgca ctttg                           35

<210> SEQ ID NO 86
<211> LENGTH: 25
<212> TYPE: DNA
<213> ORGANISM: artificial
<220> FEATURE:
<223> OTHER INFORMATION: NH2 3'

<400> SEQUENCE: 86
tgctgcttct ccaaagtgca ttatg                                      25

<210> SEQ ID NO 87
<211> LENGTH: 64
<212> TYPE: DNA
<213> ORGANISM: artificial
<220> FEATURE:
<223> OTHER INFORMATION: NR22 5'

<400> SEQUENCE: 87
gaagattttt ttttttttt tttttaata tgcagtttgt aagaacaaaa ctggatggca  60
tcag                                                             64

<210> SEQ ID NO 88
<211> LENGTH: 64
<212> TYPE: DNA
<213> ORGANISM: artificial
<220> FEATURE:
<223> OTHER INFORMATION: NR22R1 3'

<400> SEQUENCE: 88
cttctaaaaa aaaaaaaaa aaaaaattat acgtcaaaca ttcttgtttt gacctaccgt  60
agtc                                                             64

<210> SEQ ID NO 89
<211> LENGTH: 52
<212> TYPE: DNA
<213> ORGANISM: artificial

```
<220> FEATURE:
<223> OTHER INFORMATION: F1NR22-0 3'

<400> SEQUENCE: 89
ctgatgccat ccagttttgt tcttacaaac tgcatattaa aaaaaaaaaa aa            52

<210> SEQ ID NO 90
<211> LENGTH: 52
<212> TYPE: DNA
<213> ORGANISM: artificial
<220> FEATURE:
<223> OTHER INFORMATION: F1NR22-0 5'-3'

<400> SEQUENCE: 90
cagatcctct tcctccgtga gttttttttt tttttaatat gcagtttggu uc            52

<210> SEQ ID NO 91
<211> LENGTH: 50
<212> TYPE: DNA
<213> ORGANISM: artificial
<220> FEATURE:
<223> OTHER INFORMATION: F1NR22-0 3'

<400> SEQUENCE: 91
ctgatgccat ccagttttgt tcttacaaac tgcatattaa aaaaaaaaaa               50

<210> SEQ ID NO 92
<211> LENGTH: 52
<212> TYPE: DNA
<213> ORGANISM: artificial
<220> FEATURE:
<223> OTHER INFORMATION: F1NR22-0 5'-3'

<400> SEQUENCE: 92
cagatcctct tcctccgtga gttttttttt tttttaatat gcagtttggu uc            52

<210> SEQ ID NO 93
<211> LENGTH: 48
<212> TYPE: DNA
<213> ORGANISM: artificial
<220> FEATURE:
<223> OTHER INFORMATION: F1NR22-0 3'

<400> SEQUENCE: 93
ctgatgccat ccagttttgt tcttacaaac tgcatattaa aaaaaaaa                 48

<210> SEQ ID NO 94
<211> LENGTH: 52
<212> TYPE: DNA
<213> ORGANISM: artificial
<220> FEATURE:
<223> OTHER INFORMATION: F1NR22-0 3'-5'

<400> SEQUENCE: 94
cagatcctct tcctccgtga gttttttttt tttttaatat gcagtttggu uc            52

<210> SEQ ID NO 95
<211> LENGTH: 46
<212> TYPE: DNA
<213> ORGANISM: artificial
<220> FEATURE:
<223> OTHER INFORMATION: F1NR22-0 3'

<400> SEQUENCE: 95
ctgatgccat ccagttttgt tcttacaaac tgcatattaa aaaaaa                   46
```

```
<210> SEQ ID NO 96
<211> LENGTH: 52
<212> TYPE: DNA
<213> ORGANISM: artificial
<220> FEATURE:
<223> OTHER INFORMATION: F1NR22-0 5'-3'

<400> SEQUENCE: 96
cagatcctct tcctccgtga gttttttttt tttttaatat gcagtttggu uc          52

<210> SEQ ID NO 97
<211> LENGTH: 26
<212> TYPE: DNA
<213> ORGANISM: artificial
<220> FEATURE:
<223> OTHER INFORMATION: F1NR22-0 5'

<400> SEQUENCE: 97
cacggtccag atcctcttcc tccgtg                                        26

<210> SEQ ID NO 98
<211> LENGTH: 52
<212> TYPE: DNA
<213> ORGANISM: artificial
<220> FEATURE:
<223> OTHER INFORMATION: J5NR22-4 3'

<400> SEQUENCE: 98
aaaaaaaaaa aaaattatac gtcaaacatt cttgttttga cctaccgtag tc          52

<210> SEQ ID NO 99
<211> LENGTH: 46
<212> TYPE: DNA
<213> ORGANISM: artificial
<220> FEATURE:
<223> OTHER INFORMATION: J5NR22-4 5'-3'

<400> SEQUENCE: 99
ggctggacgc atcgtagagt tttttttttta atatgcagtt tgguuc                 46

<210> SEQ ID NO 100
<211> LENGTH: 50
<212> TYPE: DNA
<213> ORGANISM: artificial
<220> FEATURE:
<223> OTHER INFORMATION: J5NR22-4 3'

<400> SEQUENCE: 100
aaaaaaaaaa aattatacgt caaacattct tgttttgacc taccgtagtc              50

<210> SEQ ID NO 101
<211> LENGTH: 46
<212> TYPE: DNA
<213> ORGANISM: artificial
<220> FEATURE:
<223> OTHER INFORMATION: J5NR22-4 5'-3'

<400> SEQUENCE: 101
ggctggacgc atcgtagagt ttttttttta atatgcagtt tgguuc                  46

<210> SEQ ID NO 102
<211> LENGTH: 48
<212> TYPE: DNA
<213> ORGANISM: artificial
<220> FEATURE:
<223> OTHER INFORMATION: J5NR22-4 3'
```

```
<400> SEQUENCE: 102
aaaaaaaaaa ttatacgtca aacattcttg ttttgaccta ccgtagtc                  48

<210> SEQ ID NO 103
<211> LENGTH: 46
<212> TYPE: DNA
<213> ORGANISM: artificial
<220> FEATURE:
<223> OTHER INFORMATION: J5NR22-4 5'-3'

<400> SEQUENCE: 103
ggctggacgc atcgtagagt tttttttta atatgcagtt tgguuc                     46

<210> SEQ ID NO 104
<211> LENGTH: 46
<212> TYPE: DNA
<213> ORGANISM: artificial
<220> FEATURE:
<223> OTHER INFORMATION: J5NR22-4 3'

<400> SEQUENCE: 104
aaaaaaaatt atacgtcaaa cattcttgtt ttgacctacc gtagtc                    46

<210> SEQ ID NO 105
<211> LENGTH: 46
<212> TYPE: DNA
<213> ORGANISM: artificial
<220> FEATURE:
<223> OTHER INFORMATION: J5NR22-4 5'-3'

<400> SEQUENCE: 105
ggctggacgc atcgtagagt tttttttta atatgcagtt tgguuc                     46

<210> SEQ ID NO 106
<211> LENGTH: 25
<212> TYPE: DNA
<213> ORGANISM: artificial
<220> FEATURE:
<223> OTHER INFORMATION: JOELUX5

<400> SEQUENCE: 106
ctacgagtgg ctggacgcat cgtag                                           25

<210> SEQ ID NO 107
<211> LENGTH: 34
<212> TYPE: DNA
<213> ORGANISM: artificial
<220> FEATURE:
<223> OTHER INFORMATION: Normal 3'

<400> SEQUENCE: 107
cggagaagat tgggattaca ggcgtgagcc accg                                 34

<210> SEQ ID NO 108
<211> LENGTH: 30
<212> TYPE: DNA
<213> ORGANISM: artificial
<220> FEATURE:
<223> OTHER INFORMATION: 2' O-Me 5'

<400> SEQUENCE: 108
cggagaagat tgggattaca ggcgtgagcc                                      30
```

```
<210> SEQ ID NO 109
<211> LENGTH: 43
<212> TYPE: DNA
<213> ORGANISM: artificial
<220> FEATURE:
<223> OTHER INFORMATION: 2' O-Me 5'

<400> SEQUENCE: 109
ccattccgcc ctgtgtcggt ggcucacgcc tgtaatccct uug            43

<210> SEQ ID NO 110
<211> LENGTH: 34
<212> TYPE: DNA
<213> ORGANISM: artificial
<220> FEATURE:
<223> OTHER INFORMATION: Insertion mutation 5'

<400> SEQUENCE: 110
cggagaagat tgggattaca ggcgtgagcc accg                      34

<210> SEQ ID NO 111
<211> LENGTH: 34
<212> TYPE: DNA
<213> ORGANISM: artificial
<220> FEATURE:
<223> OTHER INFORMATION: 2' O-Me 5'

<400> SEQUENCE: 111
cggagaagat tgggattaca ggcgtgagcc accg                      34

<210> SEQ ID NO 112
<211> LENGTH: 43
<212> TYPE: DNA
<213> ORGANISM: artificial
<220> FEATURE:
<223> OTHER INFORMATION: 2' O-Me 5'

<400> SEQUENCE: 112
ccattccgcc ctgtgtcggt ggcucacgcc tgtaatccct uug            43

<210> SEQ ID NO 113
<211> LENGTH: 30
<212> TYPE: DNA
<213> ORGANISM: artificial
<220> FEATURE:
<223> OTHER INFORMATION: Normal 3'-5'

<400> SEQUENCE: 113
cggagaagat tgggattaca ggcgtgagcc                           30

<210> SEQ ID NO 114
<211> LENGTH: 31
<212> TYPE: DNA
<213> ORGANISM: artificial
<220> FEATURE:
<223> OTHER INFORMATION: Insert 1bp 3'-5'

<400> SEQUENCE: 114
cggagaagat tgggattaca ggcgtgagcc a                         31

<210> SEQ ID NO 115
<211> LENGTH: 34
<212> TYPE: DNA
<213> ORGANISM: artificial
<220> FEATURE:
<223> OTHER INFORMATION: Insert 4bp 3'-5'
```

<400> SEQUENCE: 115
cggagaagat tgggattaca ggcgtgagcc accg                                    34

<210> SEQ ID NO 116
<211> LENGTH: 43
<212> TYPE: DNA
<213> ORGANISM: artificial
<220> FEATURE:
<223> OTHER INFORMATION: Template oligonucleotide 3'

<400> SEQUENCE: 116
ccattccgcc ctgtgtcggt ggcucacgcc tgtaatccct uug                          43

<210> SEQ ID NO 117
<211> LENGTH: 27
<212> TYPE: DNA
<213> ORGANISM: artificial
<220> FEATURE:
<223> OTHER INFORMATION: JOELUX 5'

<400> SEQUENCE: 117
cacaggttct caccattccg ccctgtg                                            27

<210> SEQ ID NO 118
<211> LENGTH: 20
<212> TYPE: DNA
<213> ORGANISM: artificial
<220> FEATURE:
<223> OTHER INFORMATION: CommR5 5'

<400> SEQUENCE: 118
gaggcgaggc ggagaagatt                                                    20

<210> SEQ ID NO 119
<211> LENGTH: 21
<212> TYPE: DNA
<213> ORGANISM: artificial
<220> FEATURE:
<223> OTHER INFORMATION: AluRev 5'

<400> SEQUENCE: 119
gcctcggcct cccaaagtgc t                                                  21

<210> SEQ ID NO 120
<211> LENGTH: 51
<212> TYPE: DNA
<213> ORGANISM: artificial
<220> FEATURE:
<223> OTHER INFORMATION: Uncut 3'-5'

<400> SEQUENCE: 120
ccgcctcggc ctcccaaagt gctgggatta caggcgtgag ccaccgtttt t                 51

<210> SEQ ID NO 121
<211> LENGTH: 46
<212> TYPE: DNA
<213> ORGANISM: artificial
<220> FEATURE:
<223> OTHER INFORMATION: Cut 3'-5'

<400> SEQUENCE: 121
ccgcctcggc ctcccaaagt gctgggatta caggcgtgag ccaccg                       46

```
<210> SEQ ID NO 122
<211> LENGTH: 27
<212> TYPE: DNA
<213> ORGANISM: artificial
<220> FEATURE:
<223> OTHER INFORMATION: JOELUX 5'

<400> SEQUENCE: 122
cacaggttct caccattccg ccctgtg                                         27

<210> SEQ ID NO 123
<211> LENGTH: 39
<212> TYPE: DNA
<213> ORGANISM: artificial
<220> FEATURE:
<223> OTHER INFORMATION: AluPhB 3' phosphate

<400> SEQUENCE: 123
ccattccgcc ctgtgtcggt ggctcacgcc tgtaatccc                            39

<210> SEQ ID NO 124
<211> LENGTH: 39
<212> TYPE: DNA
<213> ORGANISM: artificial
<220> FEATURE:
<223> OTHER INFORMATION: AluMeAm 3' C7-amine

<400> SEQUENCE: 124
ccattccgcc ctgtgtcggt ggctcacgcc tgtaatccc                            39

<210> SEQ ID NO 125
<211> LENGTH: 39
<212> TYPE: DNA
<213> ORGANISM: artificial
<220> FEATURE:
<223> OTHER INFORMATION: AluAbSp 3' C3 Spacer
<220> FEATURE:
<221> NAME/KEY: misc_feature
<222> LOCATION: (19)..(19)
<223> OTHER INFORMATION: n is a, c, g, or t

<400> SEQUENCE: 125
ccattccgcc ctgtgtcgnt ggctcacgcc tgtaatccc                            39

<210> SEQ ID NO 126
<211> LENGTH: 41
<212> TYPE: DNA
<213> ORGANISM: artificial
<220> FEATURE:
<223> OTHER INFORMATION: AluHL 3'

<400> SEQUENCE: 126
ccattccgcc ctgtgtcggt ggctcacgcc tggcggaatg g                         41

<210> SEQ ID NO 127
<211> LENGTH: 39
<212> TYPE: DNA
<213> ORGANISM: artificial
<220> FEATURE:
<223> OTHER INFORMATION: AluMeMult 3' C7-amine

<400> SEQUENCE: 127
ccattccgcc ctgtgtcggu ggctcacgcc tgtaatccc                            39

<210> SEQ ID NO 128
<211> LENGTH: 43
<212> TYPE: DNA
<213> ORGANISM: artificial
```

```
<220> FEATURE:
<223> OTHER INFORMATION: AluUUG 3'

<400> SEQUENCE: 128
ccattccgcc ctgtgtcggu ugctcacgcc tgtaatccct uug            43

<210> SEQ ID NO 129
<211> LENGTH: 63
<212> TYPE: DNA
<213> ORGANISM: artificial
<220> FEATURE:
<223> OTHER INFORMATION: BRFMX5'-3'

<400> SEQUENCE: 129
cctcacagta aaataggtg attttggtct agctacagag aaatctcgat ggagtgggtc   60
cca                                                              63

<210> SEQ ID NO 130
<211> LENGTH: 75
<212> TYPE: DNA
<213> ORGANISM: Homo sapiens

<400> SEQUENCE: 130
ccagggccgc gcgctcgccg tccgccacat accgctcgta gtattcgtgc tcagcctcgt   60
agtggcgcct gacgt                                                  75

<210> SEQ ID NO 131
<211> LENGTH: 34
<212> TYPE: DNA
<213> ORGANISM: artificial
<220> FEATURE:
<223> OTHER INFORMATION: MLHJ65

<400> SEQUENCE: 131
ccattccgcc ctgtgtcgct cgccgtccgc cuug                      34

<210> SEQ ID NO 132
<211> LENGTH: 64
<212> TYPE: DNA
<213> ORGANISM: artificial
<220> FEATURE:
<223> OTHER INFORMATION: GlaI-cut DNA

<400> SEQUENCE: 132
cgctcgccgt ccgccacata ccgctcgtag tattcgtgct caccctcgta gtggcgcctg   60
acgt                                                             64

<210> SEQ ID NO 133
<211> LENGTH: 25
<212> TYPE: DNA
<213> ORGANISM: artificial
<220> FEATURE:
<223> OTHER INFORMATION: MLHRev3

<400> SEQUENCE: 133
gccactacga ggctgagcac gaata                                25
```